United States Patent
Keusenkothen et al.

(10) Patent No.: US 9,708,232 B2
(45) Date of Patent: *Jul. 18, 2017

(54) METHOD AND APPARATUS FOR CONVERTING HYDROCARBONS INTO OLEFINS

(75) Inventors: Paul F. Keusenkothen, Houston, TX (US); Frank Hershkowitz, Basking Ridge, NJ (US); Gary D. Mohr, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 225 days.

This patent is subject to a terminal disclaimer.

(21) Appl. No.: 13/993,515

(22) PCT Filed: Dec. 20, 2011

(86) PCT No.: PCT/US2011/066216
§ 371 (c)(1),
(2), (4) Date: Sep. 18, 2013

(87) PCT Pub. No.: WO2012/099680
PCT Pub. Date: Jul. 26, 2012

(65) Prior Publication Data
US 2014/0296597 A1  Oct. 2, 2014

Related U.S. Application Data

(60) Provisional application No. 61/434,417, filed on Jan. 19, 2011, provisional application No. 61/434,409, (Continued)

(30) Foreign Application Priority Data

Mar. 31, 2011  (EP) .................................... 11160757

(51) Int. Cl.
C10G 9/38 (2006.01)
C10G 9/20 (2006.01)
(Continued)

(52) U.S. Cl.
CPC ............. *C07C 5/09* (2013.01); *B01J 19/0053* (2013.01); *C10G 9/00* (2013.01); *C10G 9/002* (2013.01);
(Continued)

(58) Field of Classification Search
CPC .. C07C 11/02; C07C 9/14; C07C 2/00; C07C 11/06; C07C 6/04; C07C 2521/04;
(Continued)

(56) References Cited

U.S. PATENT DOCUMENTS 1,134,677 A   4/1915  Heinemann
1,860,624 A   5/1932  Sauerwein
(Continued)

FOREIGN PATENT DOCUMENTS

BE   722895   10/1968
DE   875198    4/1953
(Continued)

OTHER PUBLICATIONS

SRI Consulting Process Economics Program "Acetylene" Report 16 (1966) and 16A (1982).

*Primary Examiner* — In Suk Bullock
*Assistant Examiner* — Aaron Pierpont

(57) ABSTRACT

An apparatus and method are provided for processing hydrocarbon feeds. The method enhances the conversion of hydrocarbon feeds into conversion products, such as ethylene. In particular, the present techniques utilize a high-severity thermal pyrolysis reactor that exposes a feed at a peak pyrolysis gas temperature ≥1540° C. to produce a reactor product comprising ethylene and acetylene and has a $C_3^+$ to
(Continued)

acetylene weight ratio ≤0.5. Then, the method separates a product comprising tars and/or solids from at least a portion of the reactor product and converts at least a portion of the remaining reactor product into a conversion product, such as ethylene.

14 Claims, 9 Drawing Sheets

Related U.S. Application Data filed on Jan. 19, 2011, provisional application No. 61/434,411, filed on Jan. 19, 2011, provisional application No. 61/434,419, filed on Jan. 19, 2011, provisional application No. 61/434,410, filed on Jan. 19, 2011, provisional application No. 61/434,415, filed on Jan. 19, 2011, provisional application No. 61/434,413, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(51) Int. Cl.
| | | |
|---|---|---|
| C10G 9/18 | (2006.01) | |
| C10G 47/00 | (2006.01) | |
| C10G 9/00 | (2006.01) | |
| B01J 19/00 | (2006.01) | |
| C07C 2/06 | (2006.01) | |
| C07C 5/09 | (2006.01) | |

(52) U.S. Cl.
CPC ............ *C10G 9/007* (2013.01); *C10G 9/18* (2013.01); *C10G 9/20* (2013.01); *C10G 9/38* (2013.01); *C10G 47/00* (2013.01)

(58) Field of Classification Search
CPC .......... C07C 5/09; C10G 50/00; C10G 57/02; C10G 2400/20; C10G 9/20; C10G 9/38; C10G 9/00; C10G 9/18; C10G 9/007; C10G 9/002; C10G 47/00
USPC ......................................... 585/330, 324, 259
See application file for complete search history.

(56) References Cited

U.S. PATENT DOCUMENTS

| | | | |
|---|---|---|---|
| 2,319,679 A | 5/1943 | Hasche et al. | |
| 2,678,339 A | 5/1954 | Harris | |
| 2,692,819 A | 10/1954 | Hasche et al. | |
| 2,885,455 A * | 5/1959 | Hennig | C07B 61/00 422/218 |
| 2,908,625 A * | 10/1959 | Korpi | C07C 11/02 208/101 |
| 3,024,094 A * | 3/1962 | Coberly | C07C 4/04 422/218 |
| 3,093,697 A | 6/1963 | Kasbohm et al. | |
| 3,156,733 A | 11/1964 | Happel et al. | |
| 3,227,771 A * | 1/1966 | Happel | C07C 4/04 423/650 |
| 3,242,223 A | 3/1966 | Nonnenmacher et al. | |
| 3,268,615 A * | 8/1966 | Keenan, III | C07C 4/04 585/635 |
| 3,419,632 A | 12/1968 | Sogawa et al. | |
| 3,617,495 A | 11/1971 | Zimmerman, Jr. et al. | |
| 3,644,555 A | 2/1972 | Nagy et al. | |
| 3,839,484 A | 10/1974 | Zimmerman, Jr. et al. | |
| 4,274,841 A | 6/1981 | Andresen et al. | |
| 5,613,518 A * | 3/1997 | Rakieski | F16K 17/30 137/513.5 |
| 5,675,041 A | 10/1997 | Kiss et al. | |
| 5,856,592 A | 1/1999 | Hagen | |
| 6,049,011 A | 4/2000 | Kiss et al. | |
| 6,107,530 A * | 8/2000 | Hohner | C08L 91/06 106/10 |
| 6,121,503 A | 9/2000 | Janssen et al. | |
| 6,177,600 B1 | 1/2001 | Netzer | |
| 6,210,561 B1 | 4/2001 | Bradow et al. | |
| 6,307,093 B1 | 10/2001 | Godwin et al. | |
| 6,340,382 B1 * | 1/2002 | Baksh | C01B 3/56 95/117 |
| 6,578,378 B2 | 6/2003 | Kaiser et al. | |
| 7,045,670 B2 | 5/2006 | Johnson et al. | |
| 7,115,789 B2 | 10/2006 | Kuechler et al. | |
| 7,119,240 B2 | 10/2006 | Hall et al. | |
| 7,138,047 B2 | 11/2006 | Stell et al. | |
| 7,208,647 B2 | 4/2007 | Peterson et al. | |
| 7,491,250 B2 | 2/2009 | Hershkowitz et al. | |
| 7,815,873 B2 | 10/2010 | Sankaranarayanan et al. | |
| 7,846,401 B2 | 12/2010 | Hershkowitz et al. | |
| 7,914,667 B2 | 3/2011 | Keusenkothen et al. | |
| 7,943,808 B2 | 5/2011 | Hershkowitz et al. | |
| 8,106,248 B2 | 1/2012 | Keusenkothen et al. | |
| 8,158,837 B2 | 4/2012 | Mamadov et al. | |
| 8,278,231 B2 | 10/2012 | Chun et al. | |
| 8,440,070 B2 | 5/2013 | Keusenkothen | |
| 8,512,663 B2 | 8/2013 | Chun et al. | |
| 8,932,534 B2 | 1/2015 | Chun et al. | |
| 2002/0000085 A1 * | 1/2002 | Hall | B01J 8/02 60/772 |
| 2002/0098430 A1 | 7/2002 | Kawamura et al. | |
| 2004/0002553 A1 | 1/2004 | Hall et al. | |
| 2004/0192982 A1 | 9/2004 | Kuechler et al. | |
| 2005/0065392 A1 * | 3/2005 | Peterson | C07C 2/78 585/324 |
| 2007/0090018 A1 | 4/2007 | Keusenkothen et al. | |
| 2007/0090019 A1 | 4/2007 | Keusenkothen et al. | |
| 2007/0090020 A1 | 4/2007 | Buchanan et al. | |
| 2007/0191664 A1 * | 8/2007 | Hershkowitz | B01F 3/02 585/539 |
| 2008/0142049 A1 | 6/2008 | Onishi et al. | |
| 2008/0300438 A1 | 12/2008 | Keusenkothen et al. | |
| 2010/0130803 A1 | 5/2010 | Keusenkothen et al. | |
| 2010/0292523 A1 | 11/2010 | Hershkowitz et al. | |

FOREIGN PATENT DOCUMENTS

| | | |
|---|---|---|
| DE | 1270537 | 6/1968 |
| DE | 2354217 | 5/1975 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2012 |

\* cited by examiner

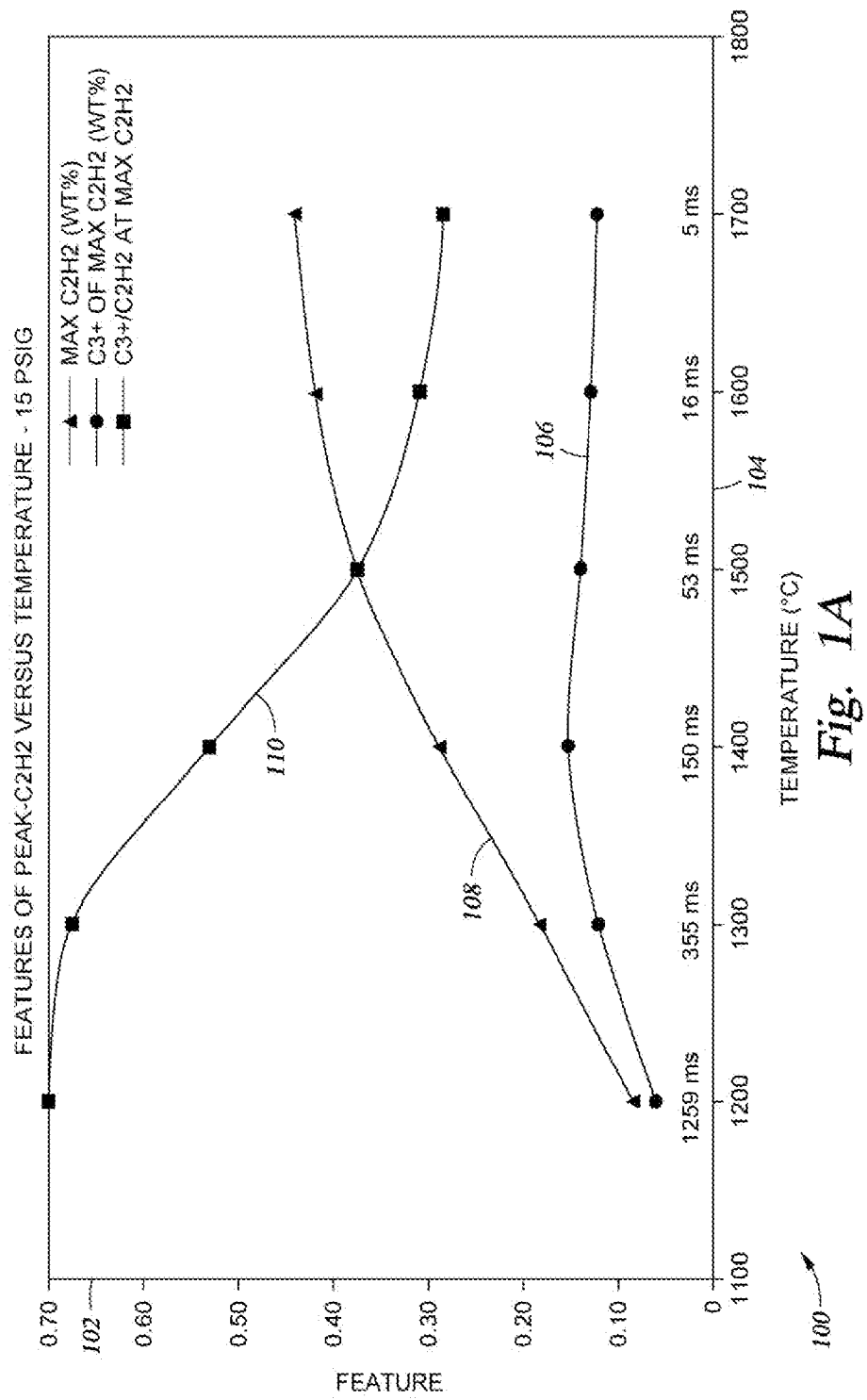

METHOD AND APPARATUS FOR CONVERTING HYDROCARBONS INTO OLEFINS

CROSS-REFERENCE TO RELATED APPLICATIONS

This application claims priority from (i) U.S. Provisional Application Ser. No. 61/434,409, filed Jan. 19, 2011, EP Application No. 11160757.8, filed on Mar. 31, 2011, and PCT/US2011/066216, filed Dec. 20, 2011; (ii) U.S. Provisional Application Ser. No. 61/434,410, filed Jan. 19, 2011, and PCT/US2011/066202, filed Dec. 20, 2011; (iii) U.S. Provisional Application Ser. No. 61/434,411, filed Jan. 19, 2011, and PCT/US2011/066210, filed Dec. 20, 2011; (iv) U.S. Provisional Application Ser. No. 61/434,413, filed Jan. 19, 2011, and PCT/US2011/066196, filed Dec. 20, 2011; (v) U.S. Provisional Application Ser. No. 61/434,415, filed Jan. 19, 2011, and PCT/US2011/066152, filed Dec. 20, 2011; (vi) U.S. Provisional Application Ser. No. 61/434,417, filed Jan. 19, 2011, and PCT/US2011/066186, filed Dec. 20, 2011; (vii) U.S. Provisional Application Ser. No. 61/434,419, filed Jan. 19, 2011, and PCT/US2011/066206, filed Dec. 20, 2011; (viii) U.S. Provisional Application Ser. No. 61/481,999, filed May 3, 2011, and PCT/US2011/066180, filed Dec. 20, 2011; (ix) U.S. Provisional Application Ser. No. 61/500,854, filed Jun. 24, 2011, and PCT/US2011/066174, filed Dec. 20, 2011; and (x) U.S. Provisional Application Ser. No. 61/504,611, filed Jul. 5, 2011, and PCT/US2011/066165, filed Dec. 20, 2011, the contents of each of which are incorporated by reference in their entirety.

FIELD

The present techniques relate to a method for converting hydrocarbons into olefins, such as ethylene, which may be further processed into the other products, such as polyolefins. Further, the present techniques relate to an apparatus used in the method, which enhances the conversion of hydrocarbons into ethylene and other products.

BACKGROUND

The oil, gas and petrochemical industry desires to efficiently obtain hydrocarbons and process the hydrocarbons to produce desired products. Refining processes involve upgrading, converting or separating hydrocarbons (e.g., crude oil) into different streams, such as gases, light naphtha, heavy naphtha, kerosene, diesel, atmospheric gas oil, asphalt, petroleum coke and heavy hydrocarbons or fuel oil. Similarly, natural gas may be converted into industrial fuel gas, liquefied natural gas (LNG), ethane, propane, liquefied petroleum gas (LPG), and natural gas liquids (NGLs). The oil and gas processes are also often integrated with petrochemical systems to convert refinery streams into chemical products, such as ethylene, propylene and/or polyolefins.

To convert hydrocarbon feeds into petrochemical or basic chemicals, chemical conversion processes may be utilized. These processes typically involve using thermal or chemical reactors or furnaces to produce reactive hydrocarbon products, such as acetylene, ethylene or propylene in different proportions. As an example, steam cracking reactors are commonly utilized to convert the hydrocarbon feed into ethylene and acetylene, which may be further processed into various chemical products. The steam cracking reactors are utilized because they provide feed flexibility by being able to utilize gas feeds (e.g., ethane) and liquid feeds (e.g., naphtha).

Historically, the oil and gas refineries utilize the higher value distillates from the hydrocarbon feed, which are typically fungible fuels, such as mogas, natural gas and diesel. As a result, the petrochemical refineries utilize the remaining fractions, such as ethane, propane, naphtha and virgin gas oil, in their processes. However, few chemical conversion processes are able to directly employ natural gas or the lower value refinery feeds, such as aromatic gas oils or fuel oils. As such, there is a need for a process that can produce ethylene and acetylene from different feeds, such as advantaged feeds (e.g., natural gas and/or aromatic gas oils).

To process these feeds, high-severity operating conditions (e.g., more severe operating conditions, such as higher temperatures) are generally used to produce products having a higher value than the feed. High-severity operating conditions enable methane cracking and aromatic ring cracking, which do not occur at appreciable rates at typical low-severity conditions (e.g., conventional steam cracking conditions). At high-severity operating conditions, the primary products of thermal chemical conversion processes are acetylene and ethylene along with hydrogen ($H_2$) and coke, which may vary in proportion depending on the temperatures, pressures, residence times and feed type utilized in the conversion process. High-severity and low-severity conversion processes are typically based on different pyrolysis reactors, which may include pyrolysis alone or integrated with combustion chemistry. That is, the reactors may include pyrolysis chemistry (e.g., thermochemical decomposition of feed at elevated temperatures in the absence of oxygen) alone or in combination with combustion chemistry (i.e., exothermic chemical reactions between a feed and an oxidant). These pyrolysis reactors can be divided into different types: partial combustion that burns part of the pyrolysis feed, indirect combustion that involves contacting the pyrolysis feed with combustion products, arc process that generate the electric arc or plasma to crack the pyrolysis feed, and thermal pyrolysis. Each of these pyrolysis types differ in the means of generating and transferring the heat for the pyrolysis, but can be broadly characterized as low-severity or high-severity.

Thermal pyrolysis reactors involve heating a solid material (e.g., by combustion) and using the heated solid material to crack the pyrolysis feed. In the thermal pyrolysis processes, the combustion products are typically maintained separate from the pyrolysis products. This pyrolysis technique involves various different types of reactors, such as a furnace (e.g., as used in steam cracking), a regenerative reactor (e.g., as used in the Wulff process) and others. For instance, thermal pyrolysis is described in various references, such as U.S. Pat. Nos. 7,138,047 and 7,119,240. U.S. Pat. No. 7,119,240 describes an exemplary process for the conversion of natural gas into ethylene. In this process, natural gas is cracked in a furnace, actively quenched, and processed in a hydrogenation reactor to produce ethylene. As another example, U.S. Pat. No. 7,138,047 describes another steam cracking process that mixes a hydrocarbon feed with a dilution steam, flashing the mixture, and vaporizing a portion of the mixture in a pyrolysis reactor. In the process, the pyrolysis feed is passed through tubes in the radiant section of a pyrolysis reactor to crack the pyrolysis feed without contaminating it with combustion products. However, due to the nature of a tubular (metal) furnace, steam cracking is limited to effective cracking temperatures of below 1000° C. and residence times of greater than or equal to (≥) 100 milliseconds (ms), which does not effectively convert either methane or aromatics, thereby limiting the feedstock selection. In addition, energy or furnace heat not used in cracking is partially lost in the furnace flue gas or in the quench, as products are quickly cooled to stop undesired reactions.

The "Wulff" reactor, as described in the IHS, SRI Consulting's Process Economics Program "Acetylene" Report Number 16 (1966) and 16A (1982), along with U.S. Pat. Nos. 2,319,679; 2,678,339; 2,692,819; 3,024,094, and 3,093,697, uses a reverse-flow pyrolysis reactor, which is operated at temperatures of less than (<) 1400° C., to produce olefins and alkynes, such as acetylene. The pyrolysis feed is heated by refractories, which have previously been heated by combustion reactions. The pyrolysis feed is cracked, and then further cooled outside of the reactor. The relatively slow quenching is a characteristic of the Wulff process that leads to coke and soot formation from using inefficient indirect heat transfer (e.g., from checker brick). Coke formation in the reactor provides fuel during the combustion cycle and excess coke or soot may be alleviated by using a light feed, i.e., a hydrocarbon containing a high proportion of hydrogen. However, because the indirect heat transfer limits the rate of heat input in the Wulff process, certain pyrolysis feeds, such as methane, may not be economically processed, which limits the feed flexibility for this process.

Further, while pyrolysis regenerative reactors have been used commercially, these reactors are not widely used for the conversion of certain feeds (e.g., natural gas or fuel oils) into acetylene or ethylene. That is, the inefficient refractories limit heat transfer (both for adding heat necessary for pyrolysis and for removing heat necessary for quenching). As a result, the Wulff reactors typically involve cracking temperatures below 1400° C. and involve the use of more expensive feeds, such as ethane, propane and naphtha. In addition, the poor heat transfer limits lead to greater soot generation resulting in poorer selectivity to desired products.

Moreover, various references describe that the reverse flow reactor is not feasible for converting methane to ethylene. In a comparison of the known acetylene conversion technologies, including the partial combustion, indirect combustion, arc processes, and thermal pyrolysis, the regenerative reactors are considered infeasible for methane to ethylene conversion due to the lower attainable temperatures in the Wulff process. That is, the Wulff process, which has checker bricks or refractory tiles within the reactor, is unable to withstand the constant temperature changes inherent in the process. Further, certain of the references describe that partial oxidation of natural gas to acetylene with heat recovery is the most economical process. These references dismiss the use or lighter feeds, such as methane, because it can not be used economically. As such, the use of a reverse flow reactor is not taught as being possible for various reasons.

Although pyrolysis reactors may be used to convert hydrocarbons into useful products, such as acetylene and ethylene, improved reactions are desired which can make use of a broader range of feeds. Accordingly, it is desirable to provide a process that converts hydrocarbon feeds into ethylene in an enhanced manner.

SUMMARY

In one aspect, one or more embodiments of the present techniques provide a hydrocarbon conversion method for converting hydrocarbons into olefins, such as ethylene. In particular, the present techniques utilize a regenerative pyrolysis reactor system to convert a hydrocarbon feed to ethylene and other petrochemical products in an enhanced manner.

A hydrocarbon conversion method comprising: (i) exposing a pyrolysis feed to thermal pyrolysis high-severity operating conditions including a peak pyrolysis gas temperature ≥1540.0° C. to produce a reactor product that comprises ethylene and acetylene and that has an $C_{3+}$ to acetylene weight ratio ≤0.5; (ii) removing from the reactor product a first product comprising tars and/or solids; and (iii) converting at least a portion of the reactor product's acetylene to ethylene, wherein the converting is downstream of the removing.

An apparatus for processing hydrocarbons comprising: (i) a thermal pyrolysis reactor configured to expose a pyrolysis feed to high-severity operating conditions including a peak pyrolysis gas temperature ≥1540.0° C. within the thermal pyrolysis reactor to produce a reactor product that comprises ethylene and acetylene and that has an $C_{3+}$ to acetylene weight ratio ≤0.5; (ii) a solid removal unit in fluid communication with the thermal pyrolysis reactor and configured to separate a bottoms product comprising tars and/or solids from the reactor product provided from the thermal pyrolysis reactor; and (iii) an acetylene converter in fluid communication with the solid removal unit and configured to convert the at least a portion of the reactor product's acetylene into ethylene.

Further, in one or more embodiments, a method for processing hydrocarbons is described. The method includes passing a pyrolysis feed to a thermal pyrolysis reactor; exposing at least a portion of the pyrolysis feed in the thermal pyrolysis reactor at a peak pyrolysis gas temperature equal to or above 1540.0° C. to produce a reactor product comprising ethylene and acetylene; separating a bottoms product comprising tars and/or solids from the reactor product; and converting at least a portion of the reactor product into a conversion product. This method may alternatively involve exposing at least a portion of the pyrolysis feed in the thermal pyrolysis reactor at high-severity operating conditions to produce the reactor product comprising ethylene and acetylene, wherein the operating conditions comprise a peak pyrolysis gas temperature equal to or above 1400.0° C. and a $C_{3+}$ to acetylene weight ratio less than or equal to (≤) 0.5. Further, the thermal pyrolysis reactor is operated at operating conditions to produce a reactor product comprising a $C_{3+}$ to acetylene weight ratio of ≤0.45, or ≤0.4, or ≤0.3. Further still, the method may include mixing other fluids, such as hydrogen, with the hydrocarbon feed to form a pyrolysis feed having a hydrogen gas to feed carbon molar ratio of 0.1 to 5.

Further still, in one or more embodiments, an apparatus for processing hydrocarbons is described. The apparatus comprises a thermal pyrolysis reactor configured to expose at least a portion of a pyrolysis feed to a peak pyrolysis gas temperature equal to or above 1540° C. within the thermal pyrolysis reactor to produce a reactor product comprising ethylene and acetylene and a solid removal unit in fluid communication with the thermal pyrolysis reactor and configured to separate a bottoms product comprising tars and/or solids from at least a portion of the reactor product. The apparatus may further include an acetylene converter in fluid communication with the solid removal unit and configured to convert at least a portion of the reactor product into an ethylene product. Further, the acetylene converter may be in fluid communication with a polymerization unit configured to convert at least a portion of the ethylene product into polyethylene.

In certain embodiments of the method or apparatus, the thermal pyrolysis reactor may be a regenerative reverse flow reactor. This reactor may include a reactor body, wherein the reactor body forms a reaction region within the reactor body; a packing material disposed at least partially within the reaction region; and one or more valve assemblies coupled to the reactor body and in flow communication with the reaction region and configured to control fluid flow of the at least a portion of the pyrolysis feed between a location external to the reactor body and within the reaction region. Further, the one or more valve assemblies may be poppet valve assemblies.

In certain embodiments of the method or apparatus, the high-severity operating conditions may include exposing the pyrolysis feed to a peak pyrolysis gas temperature from 1540.0° C. to 2200.0° C., and the residence time for the at least a portion of the pyrolysis feed within the thermal pyrolysis reactor is in the range of 0.5 seconds and 0.001 second. In other embodiments, the high-severity operating conditions may include exposing the pyrolysis feed to a peak pyrolysis gas temperatures from 1600.0° C. to 1800.0° C., and the residence time for the at least a portion of the pyrolysis feed within the thermal pyrolysis reactor is between 0.5 second and 0.001 second. The method may involve a cycle time of a combustion step and a pyrolysis step in the thermal pyrolysis reactor that is between 0.5 second to 30 seconds.

BRIEF DESCRIPTION OF THE DRAWINGS

FIGS. 1A through 1F are diagrams of simulation results representing different ratios of reactor products produced at different temperatures and/or different pressures.

Figure 1B:
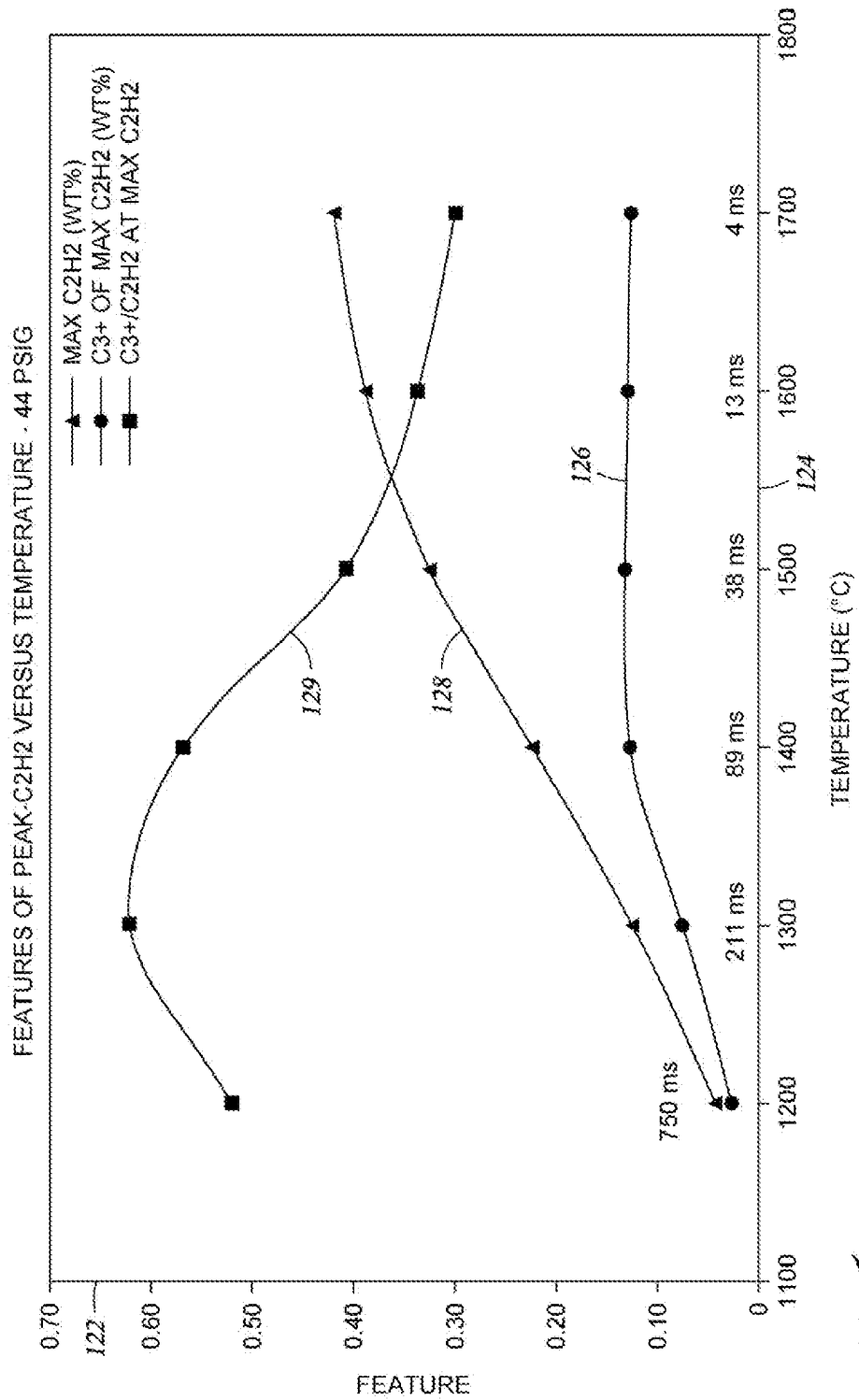

Although the invention is described in terms of a thermal pyrolysis process for producing acetylene and ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE EMBODIMENTS

In contrast to conventional techniques, the present techniques provide an enhanced process for conversion of feed containing hydrocarbons to acetylene and ethylene and optionally polyethylene. The present techniques utilize a thermal pyrolysis reactor configured to expose the pyrolysis feed to higher temperatures than conventional steam cracking. These higher temperatures are utilized to crack feeds that are normally unreactive or react to low value products (e.g., degraded products) at lower temperatures. As a specific example, at temperatures greater than or equal to (≥) 1200.0° C., methane and aromatic components are partially cracked to yield unsaturated $C_2+$ compounds, typically acetylenes and ethylene. At temperatures ≥1400.0° C., or preferably ≥1540.0° C., aromatics and methane may be cracked at high conversion levels, with selectivity levels ≥50 wt % to light gas products. That is, at atmospheric pressure, higher temperature also provides selectivity to enhance the yield of unsaturated $C_2+$ compounds (e.g., yield of ethylene and acetylene). For example, the ethylene to acetylene ratio (E/A) can be ≤0.10 or as low as 0.02 (for residence times ≤0.1 milliseconds (ms)) for increasing temperature levels at atmospheric pressure.

At any elevated temperature, hydrocarbon pyrolysis or hydropyrolysis produces acetylene at an intermediate residence time. As time continues, the hydrocarbons react further towards condensed species and eventually carbon (e.g., produce more coke). Thus, there is a maximum amount of acetylene, which is achieved at a specific residence time, and which is the optimum acetylene yield for a given temperature. The temperature and residence time of this maximum acetylene yield can be used to characterize thermal pyrolysis reactor performance at that temperature, in terms of the yield of $C_{3+}$ in relationship to the yield of acetylene. The yield of $C_{3+}$, as used herein, includes all $C_{3+}$ products of the pyrolysis feed, whether those products emerge from the reactor or remain within the reactor as coke. $C_{3+}$ includes, for example, products such as methyl acetylene, benzene and tar, and is specifically defined as including carbonaceous byproducts, such as coke.

To further explain the high-severity pyrolysis reactor and its associated products, various simulation results representing different ratios of reactor products produced at different temperatures and/or different pressures are provided. These simulations utilize certain feeds, such as methane, for simplicity, but the invention is not limited thereto. The maximum acetylene yield, the corresponding $C_{3+}$ yield and the acetylene to $C_{3+}$ ratio is described further in relation to temperature and residence time in FIGS. 1A and 1B and Table 1.

FIGS. 1A and 1B illustrate simulation results for different weight ratios of reactor products produced at different temperatures from a methane feed. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen in a methane feed, and at a pressure of 14.7 psig (101 kPag) for diagram 100 and at a pressure of 44 psig (303 kPag) for diagram 120. All hydrocarbon products larger than $C_2$ are considered as $C_{3+}$ in this example and the product is the reaction product yield from the converted pyrolysis feed. In diagram 100, certain values for maximum acetylene yield 108 in wt % of the product, and corresponding $C_{3+}$ yield 106 in weight percent (wt %) of the product, and $C_{3+}$ to acetylene weight ratio 110 of the product are shown along the Y-axis 102 for various temperatures (in ° C.) along the X-axis 104. The $C_{3+}$ to acetylene weight ratio 110 has a peak between the temperatures of 1200° C. and 1400° C., which decreases at a slower rate as temperature increases from 1500° C. or 1540° C. Similarly, in diagram 120, certain values for a maximum acetylene yield 128 in wt % of the product, and corresponding $C_{3+}$ yield 126 in wt % of the product, and $C_{3+}$ to acetylene weight ratio 129 of the product are shown along the Y-axis 122 for various temperatures (in ° C.) along the X-axis 124. The $C_{3+}$ to acetylene weight ratio 110 again has a peak within the range of 1300° C. to 1400° C., which decreases at a slower rate from 1500° C. or 1540° C. as the temperature increases. As such, operating conditions of the thermal pyrolysis reactor may be adjusted to enhance the acetylene yield for a pyrolysis feed.

This aspect is further described in Table 1, which includes simulation results for different ratios of reactor products produced at different temperatures from methane. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen (as $H_2$) in a methane feed, and at 14.7 psig (101 kPag) reactor pressure. Table 1 lists the results, such as composition of the pyrolysis product (weight percent of total pyrolysis product), for operations at temperatures between 1200° C. and 2200° C.:

TABLE 1

| | Temperature (° C.) | | | | | | | | |
|---|---|---|---|---|---|---|---|---|---|
| | 1200 | 1300 | 1400 | 1500 | 1540 | 1600 | 1650 | 1700 | 2200 |
| Max $C_2H_2$ (wt % of product) | 8.6% | 18.1% | 28.8% | 37.5% | 39.6% | 41.8% | 43.0% | 44.0% | 49.4% |
| Time of max $C_2H_2$ (sec) | 1.259 | 0.355 | 0.150 | 0.053 | 0.035 | 0.016 | 0.009 | 0.005 | 0.00006 |
| $C_{3+}$(wt % of product) | 6.0% | 12.2% | 15.3% | 14.0% | 13.7% | 12.9% | 12.6% | 12.3% | 12.9% |
| $C_{3+}/C_2H_2$ | 0.699 | 0.673 | 0.530 | 0.372 | 0.346 | 0.308 | 0.293 | 0.281 | 0.261 |
| $C_2H_2$/unit reactor volume (relative units) | 0.068 | 0.510 | 1.928 | 7.066 | 11.31 | 26.38 | 47.8 | 92.98 | 8233 |
| $CH_4$ conversion | 29.9% | 53.4% | 73.3% | 83.1% | 84.6% | 86.9% | 88.8% | 88.7% | 96.9% |
| $H_2$ (wt % of product) | 24.2% | 27.9% | 31.2% | 32.9% | 33.2% | 33.6% | 34.0% | 33.9% | 34.8% |
| Surplus $H_2$ (wt % of product) | 3.5% | 6.5% | 8.9% | 10.0% | 10.1% | 10.3% | 10.6% | 10.4% | 11.0% |

As shown in this table, the maximum acetylene yield increases rapidly with temperature until 1500° C. Above this temperature, the maximum acetylene yield increases at a slower rate. Further, the residence time required to achieve this conversion decreases with increasing temperature. For instance, at 1200° C., residence times over 1 second are needed, and acetylene comprises only about 8.6 wt % of the products, while at 1700° C., residence times of about 5 milliseconds are needed and acetylene comprises 44.0 wt % of the products. Residence time has a large impact on reactor volume (proportional to the reciprocal of residence time). As a result, a given unit of reactor may process more pyrolysis feed when the reactor temperature is high and residence time is low, which is shown in Table 1 as the $C_2H_2$/unit reactor volume. However, the very short residence times that achieve optimal acetylene yields at very high temperatures may place demands on certain reactor components that may exceed practicality. For example, where the pyrolysis feed is being flowed through the hot region of the pyrolysis reactor, the required gas velocity is roughly equal to the length of the hot region divided by the desired residence time. Gas velocities in flow channels and valve orifices are preferred to be less than the velocity of sound, which may result in reactor lengths that are not practical. In addition, because thermal pyrolysis involves the transfer of heat through a solid intermediary from a combustion step to a pyrolysis step, extremely short residence times may impose a heat transfer rate requirement (heat of reaction divided by reaction time) that may not be practical. As such, the design and operating conditions of the reactor may limit the maximum temperature that may be utilized to crack the given feed.

Even though maximum acetylene ($C_2H_2$) yield increases for methane with increasing temperature, the $C_{3+}$ yield is greatest for intermediate temperatures, such as 1400° C. Dividing $C_{3+}$ yield by acetylene yield gives a selectivity parameter ($C_{3+}/C_2H_2$) that indicates how much $C_{3+}$, which is related to coke production, has to be managed per unit of acetylene produced. This selectivity parameter remains very high (e.g., $\geq 0.5$) for temperatures below 1500° C., and drops into a lower section (e.g., $\leq 0.45$ or $\leq 0.4$) for temperatures at or above 1500° C.

For feeds containing high levels of aromatics or methane, temperatures below 1500° C. are not as effective for production of acetylene because of the high $C_{3+}$ yields, the low acetylene yields, and the relatively long residence times (e.g., large reactor volumes) needed for processing. Conversely, considering the broad range of temperature cited for methane pyrolysis, there is an advantage to operating at temperatures above 1500° C., in terms of $C_2$ unsaturate ($C_2U$) yield and $C_2$ selectivity.

In addition, as shown in Table 1, pyrolysis of hydrogen-rich feed components of the pyrolysis feed, such as methane, result in substantial yield of hydrogen ($H_2$) gas. While the feed is composed of 20 wt % $H_2$ gas, the reactor product is composed on 24 wt % to 35 wt % $H_2$ gas. Surplus hydrogen may be calculated as the amount of $H_2$ remaining after conversion to some preferred product. In Table 1, surplus $H_2$ is calculated after subtracting the stoichiometric amount of $H_2$ utilized to convert the acetylene product to ethylene. For temperatures above about 1500° C., surplus $H_2$ remains roughly constant at about 10 wt % of the reactor product. Thus, the pyrolysis of hydrogen-rich hydrocarbon components of the pyrolysis feeds results in surplus $H_2$ that is available for use in the hydrotreating and pyrolysis of hydrogen-deficient feeds or for other processes.

The high severity pyrolysis is also substantially impacted by weight ratio of hydrogen ($H_2$) gas to feed hydrocarbon carbon (C), as shown in Table 2, below. Pyrolysis, in this example, is performed under isothermal conditions, for a feed containing methane gas and optionally hydrogen gas, at a temperature of 1550° C. and at 14.7 psig (101 kPag) reactor pressure. Residence time, in each case, is selected to give 70 wt % conversion of the methane feed. Table 2 lists the results, such as composition of the pyrolysis product (weight percent of total pyrolysis product) for operations at $H_2/C$ levels between 0 and 5:

TABLE 2

| | $H_2/CH_4$ (molar ratio) | | | | | |
|---|---|---|---|---|---|---|
| | 0 | 1 | 2 | 3 | 4 | 5 |
| Residence time, sec | 0.004 | 0.007 | 0.011 | 0.014 | 0.018 | 0.021 |
| $CH_4$ Conversion: | 70.0% | 70.0% | 70.0% | 70.0% | 70.0% | 70.0% |
| $C_2U$, wt % | 28.2% | 34.7% | 36.0% | 35.1% | 33.4% | 31.6% |
| $C_{3+}$, wt % | 28.2% | 15.6% | 9.3% | 6.1% | 4.4% | 3.3% |
| Hydrogen ($H_2$), wt % | 13.5% | 23.1% | 30.7% | 37.0% | 42.2% | 46.7% |
| $C_{3+}/C_2U$ | 1.000 | 0.449 | 0.259 | 0.175 | 0.131 | 0.104 |
| relative $C_2$ productivity: | 509 | 280 | 168 | 111 | 78 | 57 |

As shown in Table 2, increasing hydrogen ($H_2$) diluent results has a small impact on $C_2U$ (e.g., acetylene and ethylene) yield, however increasing hydrogen diluent results in a substantial decrease $C_{3+}$ yield and corresponding decrease in $C_{3+}/C_2U$ weight ratio. Low hydrogen diluent levels may result in an unacceptably high level of $C_{3+}$ yield and corresponding decrease in $C_{3+}/C_2U$ weight ratio. High hydrogen diluent levels have a deleterious impact on reactor productivity because (a) the dilution reduces kinetic rates resulting in longer residence times (larger reactors) to achieve the same productivity, and (b) because $H_2$ dilution reduced the amount of hydrocarbon (and hence hydrocarbon products) that are carried in each volume of gas. These effects are reflected in the relative $C_2$ productivity entry in Table 2, which shows in relative terms the impact of hydrogen dilution on amount of $C_2$ hydrocarbons that are produced in a unit of reactor volume. High hydrogen dilution may also result in debits in process equipment outside of the pyrolysis reactor due to the larger volumes of gases that have to be managed per unit of pyrolysis product produced. Thus, there is an optimum amount of hydrogen diluent at moderate levels between 0 and 5. Accordingly, the present techniques, by means of high temperature pyrolysis, achieve at low $H_2/C$ molar ratio, a level of $C_{3+}/C_2U$ that would otherwise require operating at high (and less economical) levels of $H_2/C$.

As shown in Table 3 below, conditions and yields for the pyrolysis of hydrogen deficient feeds may be different than those for the pyrolysis of hydrogen rich feeds shown in Table 1. A hydrogen deficient feed, in this example toluene having 8.7 wt % hydrogen content, is pyrolysed at a temperature of 1445° C., a pressure of 4 psig (28 kPag), and for a residence time of 0.08 seconds; with the pyrolysis being carried out in the presence of a hydrogen diluent at a level of 28 moles $H_2$ gas per mole of hydrocarbon carbon. In this toluene conversion case, a high $H_2/C$ molar ratio is employed to compensate for a low pyrolysis temperature (1445° C.), while still achieving acceptable $C_{3+}/C_2U$ performance, thus illustrating features of toluene cracking. As indicated above, a more preferred operation would pyrolyze the toluene at higher temperature and lower $H_2/C$ molar ratio.

TABLE 3

| Pyrolysis of Toluene (8.7 wt % H) | | Products: wt % of toluene feed | | Product Ratios | wt/wt |
|---|---|---|---|---|---|
| Pressure (psig) | 4 | Methane | 26% | $C_{3+}/C_2H_2$ | 0.351 |
| Temp (C.) | 1445 | Ethylene | 12% | $C_{3+}/C_2U$ | 0.283 |
| Residence time, ms | 80 | Acetylene | 49% | E/A | 0.238 |
| $H_2/C$ | 28 | $C_{3+}$ | 17% | | |
| | | $H_2$ | −5% | | |

As shown in Table 3, the pyrolysis results in a high conversion to acetylene (49 wt %) and ethylene (12 wt %), but also yields 17 wt % $C_{3+}$ materials (mostly coke and tar). In contrast to the pyrolysis of hydrogen rich feed (Table 1), the hydropyrolysis of hydrogen deficient feed results in a consumption of hydrogen (from the $H_2$ diluent), and the production of methane (26 wt % of feed toluene) as a product. Accordingly, it is advantageous to recycle the excess hydrogen ($H_2$) and methane gas that is produced from pyrolysis of hydrogen deficient feeds to be combined into the pyrolysis feed.

While the high-severity temperatures may be preferred if the objective of the process is to produce acetylene, variations in pressure along with the high-severity temperatures may enhance the distribution of $C_2$ compounds (e.g., yield of ethane, ethylene and acetylene) and the distribution of other light hydrocarbons (e.g., propylene, propyne, etc.). Accordingly, these pressure variations may be utilized if ethylene and/or other olefins are the preferred product. As an example, steam cracking typically utilizes lower temperature to convert ethane to ethylene and trace levels of acetylene. At atmospheric pressure, lower temperatures result in higher ethylene to acetylene (E/A) weight ratios. However, lower temperatures also provide poor conversions for methane and aromatics, which as noted above, is inefficient. At high-severity conditions (e.g., temperatures ≥1400.0° C. or preferably ≥1540.0° C., for example) aromatics and methane may be cracked at high conversion levels, with selectivity levels ≥50 wt % to light gas products. Also shown in Table 1, at temperatures ≥1400° C., selectivity levels ≥50 wt % to light gas products are achievable. For example, at 1540° C., products of methane make up 67.8 wt % of the pyrolysis product, including $H_2$, $C_2$'s, and $C_{3+}$. Thus, the selectivity to $C_{3+}$ is 20 wt % (13.7 wt/67.8 wt %), and the selectivity to lighter gas products is 80 wt %. Further, by varying the pressure from atmospheric to elevated pressures (e.g., up to 300 psig (2068 kPag)), ethylene to acetylene (E/A) weight ratios ≥0.1, or ≥0.2, or ≥0.4 or even ≥0.5 may be achieved. The variations of pressure at high-severity operating conditions are described below in Tables 4 and 5 and FIGS. 1C to 1F.

Table 4 includes simulation results for different ratios of reactor products produced at different pressures for different temperatures from a methane feed. Pyrolysis, in this example, is carried out under isothermal conditions at 1500° C. and at 1650° C., with 2:1 molar diluent of hydrogen in a methane feed, and at 15 psig (103 kPag) reactor pressure to 162 psig (1117 kPag) reactor pressure. All products larger than $C_2$ are considered as $C_{3+}$ in this example, and the product is the reaction product yield from the converted pyrolysis feed.

TABLE 4

| 70% Isothermal Conversion Data | | | | Products (weight percent) | | | | | Product Ratios | | |
|---|---|---|---|---|---|---|---|---|---|---|---|
| Temp (° C.) | P (psig) | time (sec) | Conv. | $H_2$ | $CH_4$ | $C_2H_2$ | $C_2H_4$ | $C_{3+}$ | $C_2U$ | $C_{3+}/C_2U$ | E/A |
| 1500 | 15  | 0.025  | 72% | 31.1 | 22.0 | 34.2 | 2.0 | 10.7 | 36.0 | 0.30 | 0.06 |
| 1500 | 36  | 0.025  | 73% | 31.1 | 21.7 | 32.7 | 3.1 | 11.3 | 36.0 | 0.32 | 0.10 |
| 1500 | 44  | 0.025  | 72% | 31.0 | 22.1 | 31.9 | 3.5 | 11.5 | 35.0 | 0.33 | 0.11 |
| 1500 | 59  | 0.025  | 71% | 30.7 | 23.3 | 30.3 | 4.1 | 11.6 | 34.0 | 0.34 | 0.14 |
| 1500 | 74  | 0.025  | 69% | 30.4 | 24.7 | 28.6 | 4.6 | 11.7 | 33.0 | 0.35 | 0.16 |
| 1500 | 103 | 0.025  | 65% | 29.7 | 27.9 | 25.4 | 5.4 | 11.5 | 31.0 | 0.37 | 0.21 |
| 1500 | 162 | 0.025  | 57% | 28.4 | 34.3 | 20.3 | 6.3 | 10.8 | 27.0 | 0.41 | 0.31 |
| 1650 | 15  | 0.0025 | 68% | 30.4 | 25.4 | 35.0 | 1.0 | 8.2  | 36.0 | 0.23 | 0.03 |
| 1650 | 36  | 0.0025 | 71% | 30.8 | 23.6 | 35.6 | 1.5 | 8.5  | 37.0 | 0.23 | 0.04 |
| 1650 | 44  | 0.0025 | 71% | 30.8 | 23.3 | 35.6 | 1.7 | 8.6  | 37.0 | 0.23 | 0.05 |
| 1650 | 59  | 0.0025 | 71% | 30.9 | 22.9 | 35.4 | 2.0 | 8.7  | 37.0 | 0.23 | 0.06 |
| 1650 | 74  | 0.0025 | 71% | 30.9 | 22.8 | 35.2 | 2.3 | 8.8  | 37.0 | 0.24 | 0.07 |
| 1650 | 103 | 0.0025 | 71% | 30.8 | 22.9 | 34.4 | 3.0 | 8.9  | 37.0 | 0.24 | 0.09 |
| 1650 | 162 | 0.0025 | 70% | 30.5 | 24.0 | 32.5 | 4.1 | 9.0  | 37.0 | 0.25 | 0.13 |

As shown in Table 4, as pressure increases from 15 psig (103 kPag) to 162 psig (1117 kPag), $C_2U$ yields in wt % of the product are roughly constant at about 33 wt % (+/−10 wt %) for 25 milliseconds (ms) residence time at 1500° C. However, the E/A weight ratios improve over this increase in pressure. At 1650° C., the $C_2U$ yields in wt % of the product are again roughly constant at about 37 wt % (+/−10 wt %) for 2.5 ms, while the E/A weight ratio increases fourfold. Accordingly, the higher pressures tend to lead to higher E/A weight ratios. Further, the $C_{3+}$ yields in wt % of the product at these different temperatures and pressures also remain relatively constant at 12% for 1500° C. and 9% for 1650° C. As a result, the $C_{3+}$ to $C_2U$ weight ratio ($C_{3+}/C_2U$) increases at slow rate, with pressure at the lower temperature, while the higher temperatures provide a roughly constant $C_{3+}$ to $C_2$ unsaturate weight ratio.

From this table, the yield of $C_2U$ (e.g., acetylene and ethylene) may be optimized for certain operating conditions. That is, a specific pressure, temperature and residence time may be utilized to optimize the distribution of $C_2U$ yield. These operating conditions may be characterized by the $C_{3+}$ to $C_2U$ weight ratio along with an E/A weight ratio, which may be further explained in view of the FIGS. 1C and 1D.

Figure 1C:
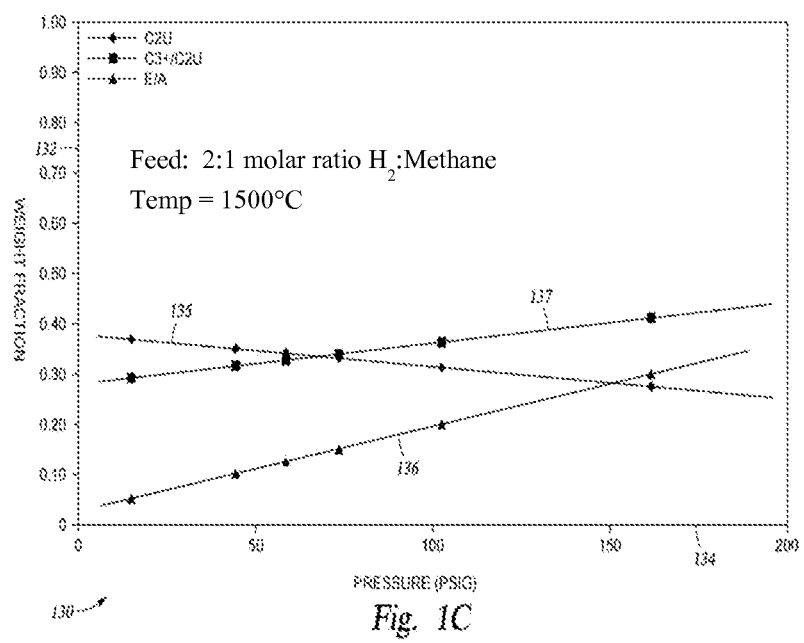
Figure 1D:
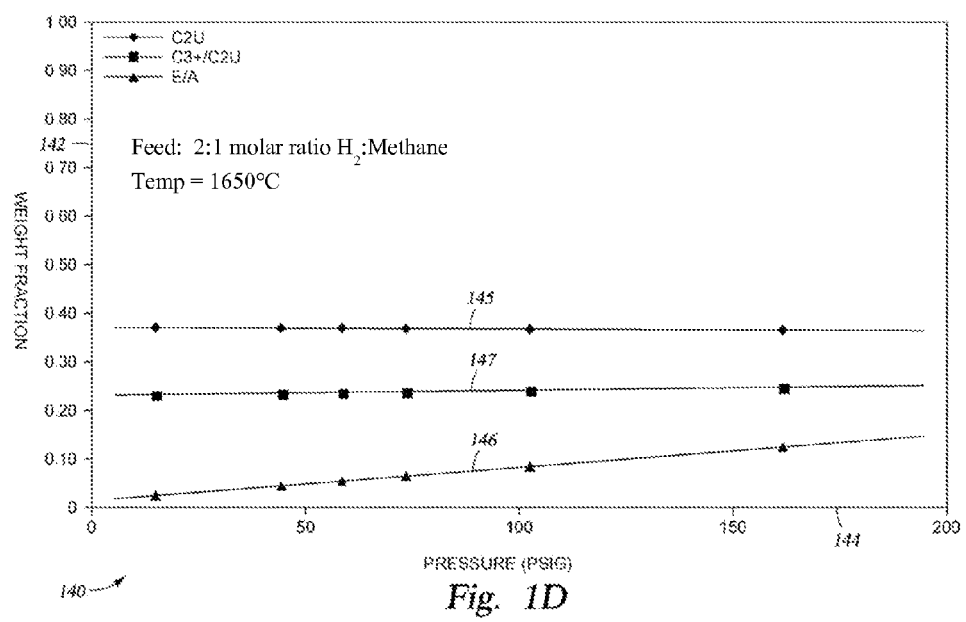

FIGS. 1C and 1D illustrate the simulation results for different ratios of reactor products produced at different pressures for certain temperatures from methane. The results of operating at the various pressures are provided for comparison of the product yields achievable at the residence times associated with the $C_2U$ yield and an E/A weight ratio for that pressure. Pyrolysis, in this example, is carried out under isothermal conditions, with 2:1 molar diluent of hydrogen in a methane feed, and at 1500° C. for diagram 130 and at 1650° C. for diagram 140. All products larger than $C_2$ are considered as $C_{3+}$ in this example and the product is the reaction product yield from the converted pyrolysis feed. In diagram 130, certain values for a $C_2U$ yield 135 in wt % of the product, ethylene to acetylene weight ratio 136, and $C_{3+}$ to $C_2U$ weight ratio 137 are shown in weight fraction (or weight ratio) along the Y-axis 132 for various pressures (in psig) along the X-axis 134. The ethylene to acetylene weight ratio 136 and $C_{3+}$ to $C_2U$ weight ratio 137 increases with increasing pressure, while the $C_2U$ yield 135 decreases slightly with increasing pressure. Similarly, in diagram 140, certain values for a $C_2U$ yield 145 in wt % of the product, ethylene to acetylene weight ratio 146, and $C_{3+}$ to $C_2U$ weight ratio 147 are shown in weight fraction (or weight ratio) along the Y-axis 142 for various pressures (in psig) along the X-axis 144. The ethylene to acetylene weight ratio 146 increases with increasing pressure, while the $C_2U$ yield 145 and $C_{3+}$ to $C_2U$ weight ratio 147 are relatively constant with increasing pressure. As such, operating conditions of the thermal pyrolysis reactor may be adjusted to enhance the acetylene yield for a given feed.

Further, as it may be appreciated, different types of thermal pyrolysis reactors may have different heat profiles. That is, some embodiments of thermal pyrolysis reactors may is operate in an isothermal manner with the heat profile being relatively constant, as noted above. However, other thermal pyrolysis reactors may have a heat profile that is similar to a Gaussian curve. For example, a regenerative reactor may be characterized by an initial and final temperature of 300° C. and a peak pyrolysis gas temperature of 1700° C. at a residence time of 35 ms (≤10 ms at temperature ≥1000° C.), the pressure effect on selectivity is even more dramatic as shown in Table 5 below.

The variations of pressure at high-severity operating conditions for a regenerative reactor are described below in Table 5 and FIGS. 1E and 1F. Table 5 includes simulation results for different weight ratios of reactor products produced at different pressures for different temperatures from a methane feed. Pyrolysis, in this example, is carried out under regenerative conditions resulting in a Gaussian-like temperature profile with inlet and outlet around 300° C. and with peak temperature of 1704° C. in one set of simulations and of 1783° C. in the other. About 25% of the residence time of the regenerative pyrolysis profile is at temperature above 1200° C. The pyrolysis of this example is carried out with 2:1 molar diluent of hydrogen in a methane feed, and at various reactor pressures between 4 psig (28 kPag) and 162 psig (1117 kPag). All products larger than $C_2$ are considered as $C_{3+}$ in this example and the product is the reaction product yield from the converted pyrolysis feed.

TABLE 5

| 70% Regenerative Conversion Data | | | | | | | | | | | |
|---|---|---|---|---|---|---|---|---|---|---|---|
| Peak | | | | Products | | | | | Product Ratios | | |
| Temp | Pres. | Time | | (weight percent) | | | | | $C_{3+}/$ | | |
| (° C.) | (psig) | (sec) | Conv. | $H_2$ | $CH_4$ | $C_2H_2$ | $C_2H_4$ | $C_{3+}$ | $C_2U$ | $C_2U$ | E/A |
| 1704 | 3 | 0.034 | 70% | 30.4 | 24.3 | 34.3 | 3.0 | 7.9 | 37.3 | 0.21 | 0.09 |
| 1704 | 15 | 0.034 | 72% | 30.7 | 22.2 | 33.6 | 5.0 | 8.4 | 38.6 | 0.22 | 0.15 |
| 1704 | 29 | 0.034 | 74% | 30.7 | 21.2 | 31.6 | 7.4 | 8.8 | 39.0 | 0.23 | 0.24 |
| 1704 | 36 | 0.034 | 74% | 30.6 | 21.0 | 30.5 | 8.5 | 8.9 | 39.0 | 0.23 | 0.28 |
| 1704 | 59 | 0.034 | 74% | 30.3 | 21.1 | 26.8 | 11.6 | 9.2 | 38.4 | 0.24 | 0.43 |
| 1704 | 103 | 0.034 | 71% | 29.4 | 23.1 | 20.1 | 15.6 | 9.1 | 35.7 | 0.26 | 0.78 |
| 1704 | 162 | 0.034 | 66% | 28.1 | 27.5 | 13.5 | 17.2 | 8.6 | 30.7 | 0.28 | 1.27 |
| 1783 | 15 | 0.011 | 67% | 30.0 | 26.5 | 33.4 | 3.0 | 7.1 | 36.3 | 0.20 | 0.09 |
| 1783 | 36 | 0.011 | 69% | 30.2 | 24.5 | 32.5 | 5.0 | 7.6 | 37.5 | 0.20 | 0.15 |
| 1783 | 44 | 0.011 | 70% | 30.2 | 24.2 | 31.9 | 5.8 | 7.8 | 37.6 | 0.21 | 0.18 |
| 1783 | 74 | 0.011 | 70% | 30.1 | 23.7 | 29.4 | 8.3 | 8.0 | 37.7 | 0.21 | 0.28 |
| 1783 | 103 | 0.011 | 70% | 29.8 | 23.8 | 26.7 | 10.6 | 8.1 | 37.3 | 0.22 | 0.40 |
| 1783 | 162 | 0.011 | 69% | 29.2 | 25.0 | 21.8 | 13.9 | 8.1 | 35.6 | 0.23 | 0.64 |

As shown in Table 5, as pressure increases from 3 psig (21 kPag) to 162 psig (1117 kPag), $C_2U$ yields decrease at a slow rate from 37 wt % to 31 wt % for a 33 ms residence time in a temperature profile that peaks at 1704° C. However, the E/A weight ratios increase rapidly with the increase in pressure. For the profile having peak temperature of 1784° C. and an 11 ms residence time, the $C_2U$ yields are roughly constant at about 37 wt %, while the E/A weight ratio again increases with increasing pressure. Accordingly, the higher pressures tend to lead to higher E/A weight ratios, while the $C_{3+}$ levels at these different temperatures and pressures remain relatively constant at around 8 wt % for the two profiles. As a result, the $C_{3+}$ to $C_2U$ weight ratio increases at slow rate for these different temperatures, with the higher temperature providing roughly constant $C_{3+}$ to $C_2U$ weight ratio, but the E/A weight ratio increases at a larger rate. Moreover, higher pressures do not have a significant impact on $C_{3+}$ levels as the $C_{3+}$ to $C_2U$ weight ratio remains almost constant, which is an enhancement over the isothermal reactors.

From this table, the regenerative reactor may be utilized to further optimize the distribution the yield of $C_2U$ (e.g., acetylene yield relative to the ethylene yield) for certain operating conditions. That is, a specific pressure, temperature and residence time may be utilized to optimize the distribution of $C_2U$ yield along with the heat profile of the reactor. These operating conditions may be characterized by the $C_{3+}$ to $C_2U$ weight ratio along with an E/A weight ratio, which may be further explained in view of the FIGS. 1E and 1F.

Figure 1E:
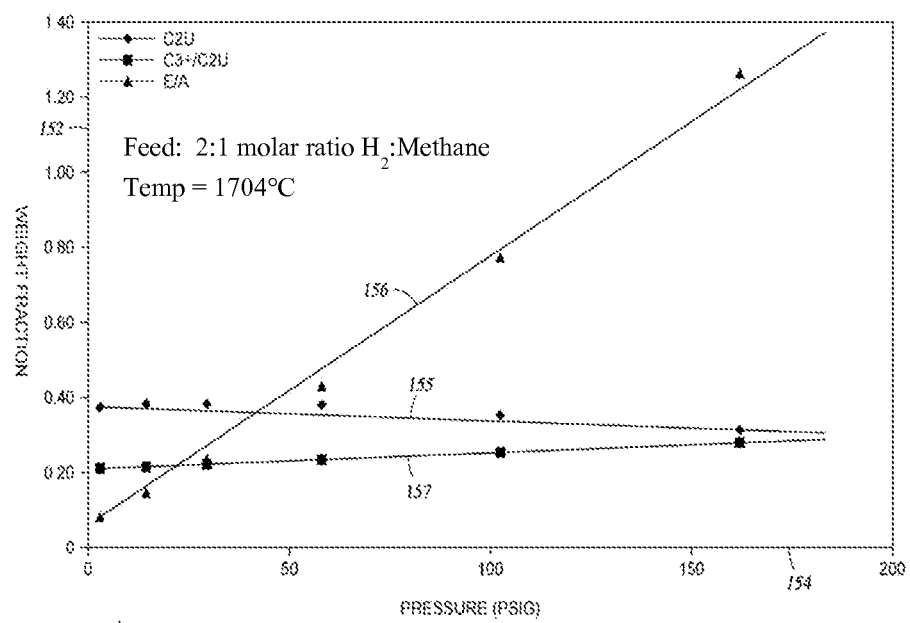
Figure 1F:
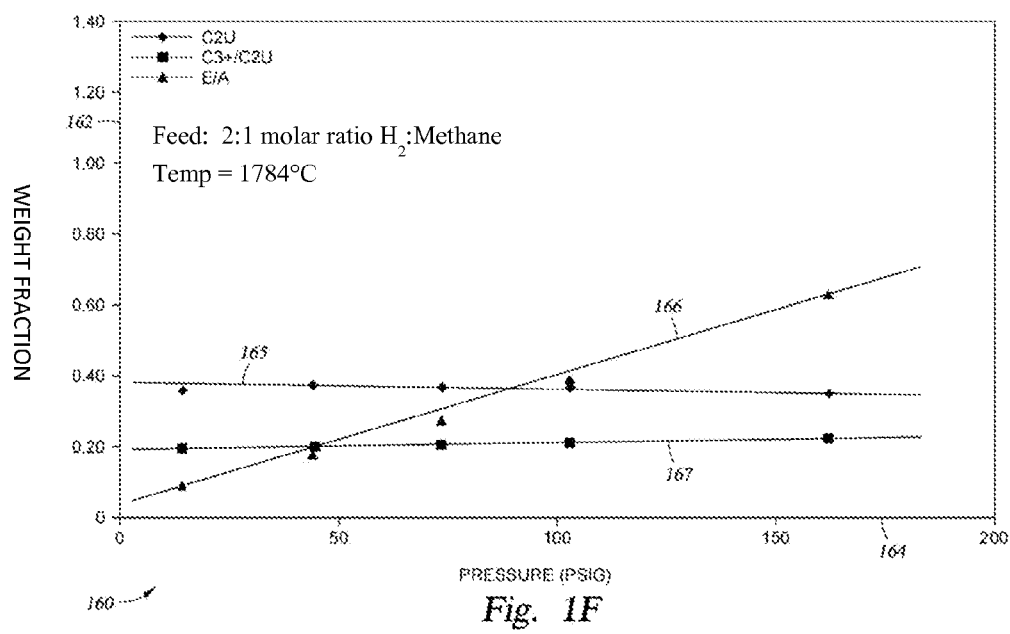

FIGS. 1E and 1F illustrate that the simulation results for different weight ratios of reactor products produced at different pressures for certain temperatures from a methane feed. The results of operating at the various pressures are provided for comparison of the product yields achievable at the residence times associated with the $C_2U$ yield and E/A weight ratio for that pressure. Pyrolysis, in this example, is carried out under regenerative reactor thermal conditions, with 2:1 molar diluent of hydrogen in a methane feed, and with a peak temperature of 1704° C. for diagram 150 and of 1784° C. for diagram 160. All products larger than $C_2$ are considered as $C_{3+}$ in this example and the product is the reaction product yield from the converted pyrolysis feed. In diagram 150, certain values for $C_2U$ yield 155 in wt % of the product, ethylene to acetylene weight ratio 156, and $C_{3+}$ to $C_2U$ weight ratio 157 are shown in weight fraction (or weight ratio) along the Y-axis 152 for various pressures (in psig) along the X-axis 154. The ethylene to acetylene weight ratio 156 and $C_{3+}$ to $C_2U$ weight ratio 157 increases with increasing pressure, while the $C_2U$ yield 155 decreases slightly with increasing pressure. Similarly, in diagram 160, certain values for $C_2U$ yield 165 in wt % of the product, ethylene to acetylene weight ratio 166, and $C_{3+}$ to $C_2U$ weight ratio 167 are shown in weight fraction (or weight ratio) along the Y-axis 162 for various pressures (in psig) along the X-axis 164. The ethylene to acetylene weight ratio 166 increases with increasing pressure, while the $C_2U$ yield 165 and $C_{3+}$ to $C_2U$ ratio 157 are relatively constant with increasing pressure. As such, operating conditions of the regenerative thermal pyrolysis reactor may be adjusted to enhance the distribution of the ethylene yield and/or acetylene yield for a given feed.

Although the E/A weight ratio continues to increase with increasing pressure, certain limiting factors may hinder higher pressure operations. For instance, eventually high pressure operating conditions may lead to unacceptable $C_{3+}$ to $C_2U$ weight ratios and/or lower $C_2U$ yields. Further, equipment utilized in the system may be limited to certain pressure ranges. Accordingly, preferred operating pressures may include pressures ≥4 psig (27 kPag), or ≥15 psig (103 kPag), or ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). As may be appreciated, these different pressures may be combined together to form different combinations depending on the specific configuration of equipment.

In addition, it is beneficial to maintain longer residence times and lower temperatures to maximize E/A weight ratio. However, such residence times and temperatures result in higher weight ratios of $C_{3+}$ to $C_2U$. Accordingly, the design and operating conditions may be adjusted to provide a balance between the E/A weight ratio and the $C_{3+}$ to $C_2U$ weight ratio. That is, the thermal pyrolysis reactor may be operated at lower temperatures to maximize the E/A weight ratio at an efficient and operable $C_{3+}$ to $C_2U$ weight ratio. Alternatively, when lower weight ratios of E/A are preferred, the reactor may be operated at higher temperature and at lower pressure to minimize the E/A weight ratio at an efficient and operable $C_{3+}$ to $C_2U$ weight ratio. As an example, the operating conditions, such as the peak pyrolysis gas temperatures and/or pressure, of the thermal pyrolysis reactor may be adjusted based on an optimized value from an optimization function that comprises an ethylene to acetylene weight ratio and the $C_{3+}$ to $C_2$ unsaturate weight ratio.

The thermal pyrolysis reactor may be limited to certain pressures by various limitations. For instance, at higher pressures and constant residence times, mass density of the gas increases and thus requires higher heat transfer rates per unit of reactor volumes. This heat transfer rate may exceed the capability of the reactor internals or may lead to exceedingly small channels or exceedingly large numbers of channels per square inch (CPSI). Thus, these limitations may eventually lead to impractical reactor dimensions and impractically high levels of pressure drop.

Unless otherwise stated, all percentages, parts, ratios, etc., are by weight. Unless is otherwise stated, a reference to a compound or component includes the compound or component by itself, as well as in combination with other compounds or components, such as mixtures of compounds. Unless otherwise stated, all pressures are given as gauge, that is, as pressure above ambient atmospheric pressure (e.g., psig).

Further, when an amount, concentration, or other value or parameter is given as a list of upper preferable values and lower preferable values, this is to be understood as specifically disclosing all ranges formed from any pair of an upper preferred value and a lower preferred value, regardless whether ranges are separately disclosed.

The terms "convert" and "converting" are defined broadly herein to include any molecular decomposition, cracking, breaking apart, conversion and/or reformation of organic molecules (hydrocarbons) in the feed, by means of at least pyrolysis heat, and may optionally include supplementation by one or more of catalysis, hydrogenation, diluents and/or stripping agents.

As used herein, the expression "non-volatiles" may be defined broadly herein to mean substantially any resid, metal, mineral, ash, ash-forming, asphaltenic, tar, coke and/or other component or contaminant within the feedstock that does not vaporize below a selected boiling point or temperature and which, during or after pyrolysis, may leave an undesirable residue or ash within the reactor system, which is difficult to remove. Non-combustible non-volatiles may include ash, for example. Methods for determining asphaltenes and/or ash may include American Society of Testing and Materials (ASTM) methods, such as methods for asphaltenes may include ASTM D-6560 and D-7061 and methods for ash may include ASTM D-189, D-482, D-524 and D-2415.

As used herein, the terms "coke" and "soot" may refer to hydrocarbonaceous material that accumulates within the reactor during pyrolysis or to solid-phase hydrocarbonaceous materials that emerge from the reactor with pyrolysis effluent. The hydrocarbonaceous material that accumulates within the reactor during pyrolysis may also be defined as the fraction of the pyrolysis feed that remains in a thermal pyrolysis reactor and thus does not emerge from the reactor as pyrolysis effluent. Coke and soot are components of the reactor product, which are included for $C_{3+}$ product for pyrolysis selectivity. The terms "$C_{3+}$ and $C_3^+$" mean all products of the pyrolysis feed having more than three carbon atoms, which include coke and soot, whether those products emerge from the reactor or remain within the reactor. The reactor product that does emerge may be referred to as the reactor effluent, which is at least a portion of the reactor product.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and optional addition of diluents).

As used herein, the "hydrocarbon feed" contains hydrocarbons (C bound to H) and may contain (i) minor components of heteroatoms (<10 wt %) covalently bound to hydrocarbons and (ii) minor components of heteroatoms (<10 wt %) not bound to hydrocarbons (e.g., $H_2O$), wherein these weight percents are based on the weight of the hydrocarbon feed. The term "hydrocarbons in the hydrocarbon feed" or "hydrocarbons of the hydrocarbon feed" means molecules within the hydrocarbon feed that contain at least hydrogen and carbon and, optionally, heteroatoms covalently bound to a portion of such molecules. Weight percents of hydrogen and carbon, as used to characterize the hydrocarbon feed, are provided as a percent of the hydrocarbons in the hydrocarbon feed. The hydrocarbon feed may include, by way of non-limiting examples, one or more of Fischer-Tropsch gases, methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter, and/or any mixtures thereof.

As used herein, the expression "advantaged feed" means a feed that has a lower cost (per ton or per heating value) than Brent reference crude oil and may include, by way of non-limiting examples, one or more methane containing feeds and one or more high-aromatic containing streams. Some examples may include one or more of Fischer-Tropsch gases, methane, methane containing streams such as coal bed methane, biogas, associated gas, natural gas and mixtures or components thereof, steam cracked gas oil and residues, gas oils, coker naphtha, steam cracked naphtha, catalytically cracked naphtha, hydrocrackate, reformate, raffinate reformate, natural gasoline, Fischer-Tropsch liquids, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, and/or any mixtures thereof.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed or reactor feed are expressed as a weight percent of hydrocarbons in the respective feed. A hydrocarbon feed may have a hydrogen content in the range of 6 wt % (weight percent) to 25 wt %, 8 wt % to 20 wt % (e.g., not natural gas), or 20 wt % to 25 wt % (e.g., natural gas). The hydrocarbon feed may be provided directly as the pyrolysis feed, may optionally be mixed with a diluent feed to form the pyrolysis feed, or may have a portion of the hydrocarbon feed removed (e.g., removal of non-volatiles at the operating conditions of the reactor) to form the pyrolysis feed. That is, the pyrolysis feed may be derived from the hydrocarbon feed. The pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2/C$) in the pyrolysis feed may be from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of the pyrolysis feed may result in a weight percent of total hydrogen in the pyrolysis feed that is greater than that in the hydrocarbon feed. For example, the weight percent of total hydrogen in the pyrolysis feed may be between 8 wt % and 54 wt %.

As used herein, the expression "combustion feed" means the two or more individual feeds that are to be combined to form a combustion reaction or a mixture of two or more feeds, such as a combustion fuel that does not contain oxidants (e.g., $O_2$) or non-combustible non-volatiles and a combustion oxidant that may include an oxygen or oxygen containing fluid. The combustion fuel may include, by way of non-limiting examples, one or more of Fischer-Tropsch gases, methane, methane containing streams such as coal bed methane, biogas, associated gas, natural gas and mixtures or components thereof, synthesis gas (mixtures of CO and $H_2$) and hydrogen. The combustion oxidant may include, but are not limited to, air, oxygen or mixtures thereof. Any of the combustion feed, fuel, or oxidant may additionally include non-combustible but volatile diluents, such as $N_2$, $CO_2$, $H_2O$, and/or other inert gases.

The term "reactor", as used herein, refers to equipment used for chemical conversion. As such, several items identified as reactors may be combined to become a single entity that is also identified as a reactor, in that individual and combined entities may all be characterized as equipment used for chemical conversion. The regenerative reverse-flow thermal pyrolysis reactors described herein may comprise first and second reactor entities, for example as described in U.S. Patent App. Pub. No. 2007/0191664.

The term "pyrolysis reactor", as used herein, refers to a system for converting hydrocarbons by means of at least pyrolysis chemistry. The pyrolysis reactor may include one or more reactors and/or associated equipment and lines. A region, as used herein, refers to a location within the pyrolysis reactor, which may include one or more reactors and/or associated equipment and lines. The region may include a specific volume within a reactor, a specific volume between two reactors and/or the combination of different disjointed volumes in one or more reactors. The regenerative reverse-flow thermal pyrolysis reactors described herein may comprise first pyrolysis reactor and second pyrolysis reactor, for example as described in U.S. Patent App. Pub. No. 2007/0191664.

As used herein, the "thermal pyrolysis reactor" includes at least predominantly pyrolysis chemistry. Pyrolysis or pyrolysis chemistry, such as the conversion of hydrocarbons to unsaturates such as ethylene and acetylene, is an endothermic process requiring addition of heat. The terms crack and cracking may be used interchangeably with the terms pyrolyse and pyrolysis. In a thermal pyrolysis reaction, ≥50%, ≥80%, or ≥90%, of this heat is provided by heat transfer via solid surfaces such as tubulars or bed materials. Any combustion chemistry that occurs within the pyrolysis stream of a thermal pyrolysis reactor provides a minority of the endothermic heat of pyrolysis, such as <50%, <20%, or <10% of the endothermic heat of pyrolysis.

The term "high-severity operating conditions" means pyrolysis conditions resulting in the conversion of the a pyrolysis feed comprising hydrocarbons to make a product having an acetylene content ≥10.0 wt % based on the weight of the hydrocarbons in the pyrolysis feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time ≤0.1 sec (second) to make at least 10 wt % acetylene as a percent of the hydrocarbons in the feed evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of methane at a pressure of 14.7 psig (101 kPag) and with 2:1 molar ratio of hydrogen diluent, the threshold temperature is about 1274° C. for this process. At temperatures at or above 1274° C., yields of acetylene can exceed 10 wt % of the starting methane, at some time ≤0.1 seconds. Conversely, at temperatures below 1274° C., there are no times ≤0.1 seconds for which yields of acetylene reaches 10 wt % of the starting methane.

According to one or more embodiments of the present techniques, an enhanced process is provided for the production of $C_2U$ (e.g., acetylene and ethylene), which are useful for manufacturing polyolefins and other petrochemical products. The process may include various stages, such as feed preparation, pyrolysis, recovery and further processing, such as separation of the polymer grade monomer and polymerization to polyethylene. A thermal pyrolysis reactor may be utilized to expose a pyrolysis feed to peak pyrolysis gas temperatures equal to or above 1540.0° C. Optionally, the thermal pyrolysis reactor may have operating conditions that are below a specific selectivity threshold, such as a $C_{3+}$ to acetylene weight ratio ≤0.5, or ≤0.45, or ≤0.4. Operation at low levels of $C_{3+}$/acetylene is desirable both to improve process economics and to improve process operability. Economics are improved by low $C_3^+$/acetylene ratio because $C_{3+}$ products produced by high-severity pyrolysis are less valuable than the acetylene product. Further, operability is improved by low $C_{3+}$/acetylene ratio because $C_{3+}$ products may include substantial amounts of coke, whose production may hinder operations. Specifically, coke produced in excess amounts may result in an inability to maintain the thermal pyrolysis reactor channels available for fluid flow, and coke produced in excess amounts may result in heat release (during combustion or regeneration steps), which is greater than the heat amounts that can be used in the process or reactor. At least a portion of the reactor product may be further processed to recover polyethylene, polyolefins, benzene or other final products.

The present techniques may involve operating the thermal pyrolysis reactor at different operating conditions. These operating conditions may include adjusting operational settings to adjust the pressure within the reactor and/or the temperature within a reactor. The operational settings may include increasing the heat generated by providing different combustion feeds to the thermal pyrolysis reactor. The present techniques may be further understood with reference to FIGS. 2 to 4, which are discussed below.

Figure 2:
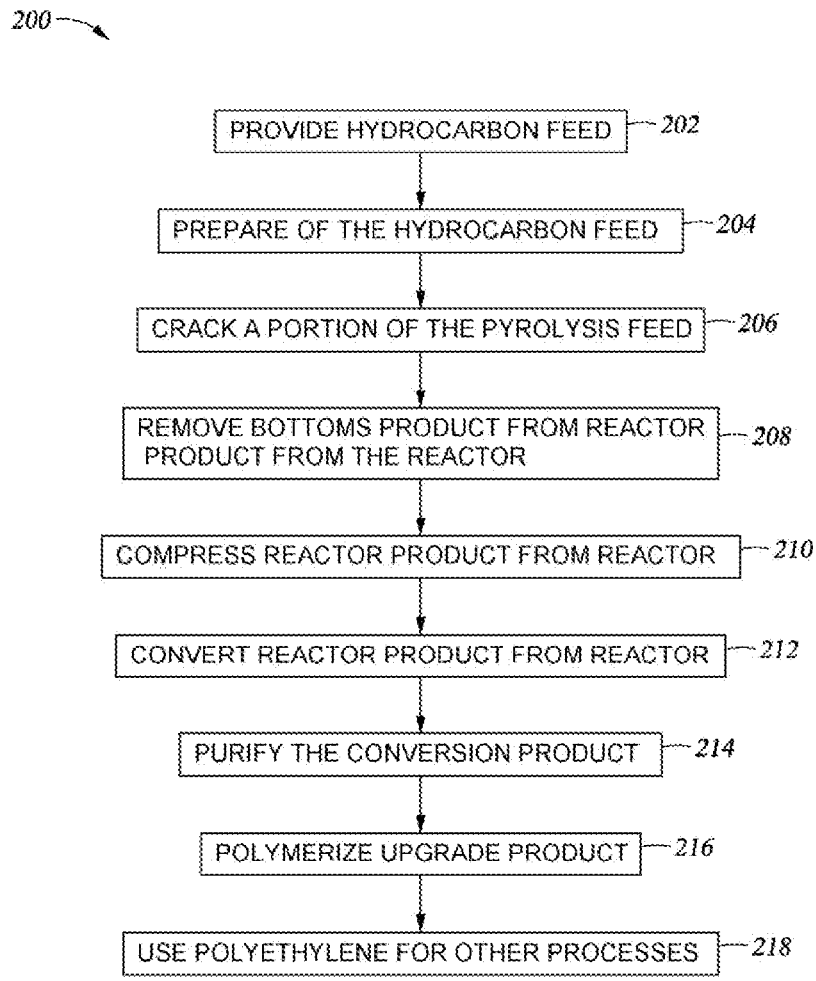
FIG. 2 is a simplified process flow diagram illustrating an embodiment of the present techniques.

To begin, an exemplary embodiment of the present techniques is illustrated in the block flow diagram 200 of FIG. 2. In this flow diagram 200, a process for the production of ethylene and subsequent conversion of the ethylene to polyolefins, such as polyethylene, is shown. In this block diagram, the process includes various stages. For instance, a feed preparation stage is described in block 204. A cracking stage is described in block 206, which involves cracking the pyrolysis feed in a thermal pyrolysis reactor, which produces a reactor product. The reactor product may contain an acetylene amount that reflects a pyrolysis $C_{3+}$/acetylene ratio of ≤0.5, or ≤0.45, or ≤0.4 or ≤0.3. The $C_2U$ components (e.g., acetylene and ethylene) of the reactor product may represent ≥50 wt %, or ≥80 wt %, or preferably ≥90 wt % of the total $C_2^+$ gas phase components of the reactor product. Then, a recovery stage is described in blocks 208 to 214, which further processes the reactor product or reactor effluent to provide ethylene. Finally, a polyethylene polymerization stage may be performed as described in block 216.

At block 202, a hydrocarbon feed is provided. The hydrocarbon feed may include one or more of methane, natural gas, petroleum or petrochemical liquids and mixtures thereof, or other suitable hydrocarbon feeds, as noted above. At block 204, the hydrocarbon feed may be subjected to various feed preparation processes to form the pyrolysis feed or may be provided directly to the thermal pyrolysis reactor as the pyrolysis feed. That is, the pyrolysis feed may be derived from the hydrocarbon feed. For example, the feed preparation processes optionally include removal of impurities or contaminants prior to cracking. The feed preparation process may include mixing the hydrocarbon feed with a diluent feed. The feed preparation processes may include one or more of condensate and water removal units, acid gas removal units (e.g., caustic or amine treater units), dehydration units (e.g., glycol units), nitrogen removal units, hydrogenation, demetalation, visbreaking, coking and/or vapor/liquid separators. The impurities or contaminants, which may include one or more of carbon dioxide, carbon monoxide, sulfur species, oxygenates and non-volatiles (e.g., metal), may be conducted away from the process.

In a preferred embodiment, the hydrocarbon feed may include non-volatiles, which are materials that are not in the gas phase (i.e. are components that are in the liquid or solid phase) at the temperature, pressure and composition conditions of the inlet to the pyrolysis reactor. Non-combustible non-volatiles (e.g., ash; ASTM D-189) are preferably limited to ≤2 parts per million weight (ppmw) on hydrocarbon feed, more preferably ≤1 ppmw. Combustible non-volatiles (e.g., tar, asphaltenes, ASTM D-6560) may be present at concentrations below 5% of the hydrocarbon feed, preferably at concentrations below 1%, more preferably at concentrations below 100 ppmw, and most preferably at concentrations below 10 ppmw of the total feed to the pyrolysis reactor, as long as the presence of the combustible non-volatiles do not result in excessive (e.g., ≥2 or ≥1 ppmw) concentrations of non-combustible non-volatiles. As a first example, the hydrocarbon feed may comprise crude oil and crude oil components. As a second example, the pyrolysis feed may comprise substantially methane (e.g., ≥50 wt %, ≥75 wt %, or ≥90 wt % of the pyrolysis feed).

After the feed preparation stage, the pyrolysis feed is cracked in block 206. The cracking of the pyrolysis feed may involve the use of a thermal pyrolysis reactor to convert the pyrolysis feed into a reactor product. The reactor product includes one or more $C_2U$, and optionally includes hydrogen ($H_2$), methane, ethane, methyl acetylene, diacetylene, and $C_{3+}$ products (e.g., benzene, tars, soot, etc.). The reactor product includes components that emerge from the reactor and those that remain within the reactor, if any, as a result of pyrolysis (e.g., coke may remain in the reactor and later emerge as a portion of the combustion products). The amount of coke remaining in the reactor may be determined from a mass balance of the process. Further, in block 206, the thermal pyrolysis reactor may include any of a variety of thermal pyrolysis reactors, such as a regenerative reverse flow reactor, as described in U.S. Patent App. Pub. No. 2007/0191664. Other embodiments may include a thermal pyrolysis reactor, as described in U.S. Pat. No. 7,491,250, U.S. Patent Ser. No. 61/349,464 and U.S. Patent App. Pub. Nos. 2007/0144940 and 2008/0142409. Regardless of the specific type of thermal pyrolysis reactor, it may operate at peak pyrolysis gas temperatures between 1200.0° C. and 2200.0° C., preferably between 1400.0° C. and 1900.0° C., such as at peak pyrolysis gas temperatures of at least 1200.0° C., at least 1400.0° C., at least 1500.0° C., at least 1540.0° C., at least 1700.0° C. In particular, for reactors with an isothermal heat profile, the temperatures may be between 1450.0° C. and 1700.0° C., or between 1540.0° C. and 1650.0° C. For reactors with a Gaussian like heat profile, the peak pyrolysis gas temperatures may be between 1450.0° C. and 1900.0° C. or 1540.0° C. and 1800.0° C. Further, the preferred operating pressures may include pressures ≥4 psig (28 kPag), or ≥15 psig (103 kPag), or ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). As may be appreciated, these different pressures and temperatures may be combined together to form different combinations depending on the specific configuration of equipment. Further, for a regenerative reverse flow reactor, the pressure in the pyrolysis step may be similar or different to the pressure in the combustion step (e.g., at lower or higher pressure than the pyrolysis step).

At least a portion of the reactor product may be conducted away for storage or further processing. Optionally, one or more upgrading processes may be included in the recovery stage, as shown in blocks 208 to 214. At block 208, the at least a portion of the reactor product may be subject to a solid removal or separation process to provide a bottoms product. The separation process may remove one or more bottom products comprising solids, such as higher boiling point materials (e.g., contaminates, solids or impurities) from the $C_2U$ in reactor product. The separation process may include a tar and/or solid removal process, compression, adsorption, distillation, washing, and drying of the reactor product, and/or any combination of one or more of these processes. Then, at block 210, the remaining reactor product may be compressed. The compression may include compressors that operate at outlet pressures pressure from 50 pounds per square inch gauge (psig) to 400 psig, or more preferably from 150 psig to 300 psig.

At block 212, the remaining reactor product may optionally be provided to a conversion process, such as an acetylene conversion process. The remaining reactor product may be in liquid phase, vapor phase or a mixture thereof, and may be subjected to a conversion process that is performed by a catalyst in the liquid phase, vapor phase or a mixture thereof. For instance, the acetylene conversion process may include acetylene hydrogenation in an isothermal, slurry or adiabatic catalytic reactor, or other suitable conventional techniques. The catalytic reactor may employ group VI or VIII catalyst, catalyst bimetal or trimetal blends on an alumina, silica or other support, is well known in the art. For example, the acetylene in the reactor product may be absorbed into a liquid, hydrogenated within that liquid and then the ethylene product is desorbed from the liquid. At block 214, conversion products, which include ethylene, may optionally be provided to a purification process. The purification process may include (multistage) distillation or refrigerated distillation, including a demethanator tower and $C_2$ splitter.

Should additional upgrading or purification of the conversion products be desired, purification systems, such as that found in *Kirk-Othmer Encyclopedia of Chemical Technology*, 4th edition, Volume 9, John Wiley & Sons, 1996, pg. 894-899, may be used. In addition, purification systems, such as that described in *Kirk-Othmer Encyclopedia of Chemical Technology*, 4th edition, Volume 20, John Wiley & Sons, 1996, pg. 249-271, may also be used. Other examples may be found in U.S. Pat. Nos. 6,121,503; 5,960,643; 5,364,915; 5,238,892; 5,280,074; 5,288,473; 5,102,841; 4,956,426; 4,508,842; and EP Patent Nos. 0612753 and 0012147.

Optionally, the upgraded product is conducted away for storage or for further processing, such as conversion into polyethylene. At block 216, the ethylene polymerization may include both the gas phase and solution polymerization methods, which conventional processes may be employed in the practice of the present techniques. As an example, U.S. Pat. Nos. 6,822,057; 7,045,583; 7,354,979 and 7,728,084 describe different ethylene polymerization processes that may be utilized.

Optionally, the conversion product may be provided for other processes or used commercially as a product. These processes may include generating ethylene glycol or other products. As an example, the conversion product (e.g., ethylene product) may be treated, separated and polymerized to form plastic compositions, which may include polyolefins, particularly polyethylene. Any conventional process for forming polyethylene may be used, while catalytic processes are preferred. Particularly preferred are metallocene, Ziegler/Natta, aluminum oxide and acid catalytic systems. Examples may include U.S. Pat. Nos. 3,258,455; 3,305,538; 3,364,190; 5,892,079; 4,659,685; 4,076,698; 3,645,992; 4,302,565 and 4,243,691. In general, these methods involve contacting the conversion product, such as ethylene, with a polyolefin-forming catalyst at a pressure and temperature effective to form the polyolefin product.

Beneficially, the proposed process provides various enhancements over previous techniques. For instance, the process provides flexibility in managing byproducts or contaminants. That is, the process may be operated in a manner that does not involve additional stages to remove various contaminants, which enhances the efficiency of the process. As an example, typical high-severity pyrolysis processes, such as partial combustion, typically utilize oxygen in the reaction with the pyrolysis feed, which produces carbon monoxide and carbon dioxide in the reactor product. By not utilizing an oxygen containing stream in the pyrolysis stage of the present techniques, various impurities, such as CO and $CO_2$, are not inherently present in the reactor product, which reduces the costs and difficulties in managing these through the process.

Also, the process may manage impurities based on the operating conditions of the thermal pyrolysis reactor. That is, the present techniques expose the pyrolysis feed to specific operating conditions that may be used to manage the production of coke. These operating conditions may include peak pyrolysis gas temperatures $\geq 1540.0°$ C. and/or high-severity operating conditions. These operating conditions may comprise a peak pyrolysis gas temperature equal to or above $1400.0°$ C. and a $C_{3+}$ to acetylene weight ratio $\leq 0.45$ or others, as noted above. These operating conditions may be adjusted to manage $C_{3+}$ production in the reactor process. As an example, certain impurities in the feed (e.g., asphaltenes and/or mercaptans) may be provided to the reactor and converted into acetylene or ethylene. By exposing the feed to these operating conditions, the $C_{3+}$ product, which may include coke, tar and/or coke precursors, may be burned off within the reactor and removed from the process. As a result, feeds with higher asphaltene contents may be managed through the system without the concerns of coking in conventional processes. Other impurities, which may include, but are not limited to, sulfur and nitrogen containing compounds, oxygenates, Hg, salts, water, $H_2S$, $CO_2$, and $N_2$, may be removed as different products prior to or after the thermal pyrolysis reactor. That is, unlike other processes, the present techniques utilize operating conditions and the thermal pyrolysis reactor to manage the impurities.

In addition, as noted above, by using high-severity conditions (e.g., higher temperatures) in the pyrolysis stage of the process, the present techniques may enhance $C_2$ selectivity. That is, the pyrolysis stage may crack the pyrolysis feed at residence times that are lower than other lower temperature processes. As a result, the pyrolysis feed is more efficiently cracked and the reactor size may be smaller (e.g., less capital expense and more efficient).

Further still, using high-severity condition of the thermal pyrolysis reactor provides greater flexibility in the pyrolysis feed utilized in the reactor. That is, the pyrolysis feed may be derived from a broader range of hydrocarbon feeds with lower hydrogen contents and advantaged feeds (e.g., heavy aromatic to methane). These advantaged feeds, which do not typically react in at low-severity condition or react to lower value products, react in the process to provide $C_2U$. Higher severity, as provided in the present process, converts at high levels aromatic containing and/or methane containing feeds to valuable $C_2$ products. As such, the process may utilize a broad range of hydrocarbon feeds that foul or are unreactive in other process.

Moreover, when the thermal pyrolysis reactor is a regenerative reverse flow reactor, the configuration may be used to control the temperature of the reactor product at the reactor outlet to a temperature between $300°$ C. to $500°$ C. That is, the process may utilize passive quenching of the process to provide a reactor product that does not have to involve active quenching steps to lower the reactor product temperature.

In addition, for one or more other embodiments of regenerative reverse flow reactors, air may be utilized instead of oxygen gas as part of the combustion process to generate heat for the pyrolysis feed because the combustion step is a separate step from the reaction step. Accordingly, this reactor may reduce capital costs and operational costs by not requiring an oxygen feed (e.g., oxygen purification facilities) and reducing units that are utilized to remove combustion products from the hydrocarbon effluent.

Further, the process may optionally involve other processing steps, such as separation steps that divide at least a portion of the reactor product into an acetylene-rich product or stream and an acetylene-lean product or stream, which may involve separating different products from the at least a portion of the reactor product in the recovery stage. The acetylene-rich product may include ≥50 wt % of the acetylene from the reactor product, ≥70 wt % of the acetylene from the reactor product, ≥85 wt % of the acetylene from the reactor product, or even ≥95 wt % of the acetylene from the reactor product. The acetylene-lean product may include from 0 wt % to the remaining portion of the acetylene that is not in the acetylene-rich product. The remaining reactor product may pass through one or more separations, such as a light gas separation or a heavier separation, to remove different products.

For example, after block 210 and prior to block 214, different light gas products (e.g., a portion of the light gas in the reactor product from the reactor) may be separated as light gas products and the remaining reactor product may form an acetylene-rich product. The light gas removal process may include different separation mechanisms along with a basic wash, for example caustic wash or amine scrubbing, to conduct the light gas products away from the remaining reactor product. For other embodiments, the light gas separation mechanisms may include pressure swing adsorption, membranes, cryogenic distillation, electrochemical separation, liquid absorption, and/or liquid phase absorption and light gas desorbtion. The membrane inlet pressure or the pressure swing adsorption inlet pressure may be between 150 psig (1034 kPag) and 250 psig (1724 kPag), while the liquid phase absorption and light gas desorbtion may be performed at pressures between 50 psig (345 kPag) and 250 psig (1724 kPag). The light gas separation mechanisms may be used to separate hydrogen, carbon monoxide, methane, nitrogen or other light gases. The light gas products, such as hydrogen and/or methane, separated from the remaining portion of the reactor product may be used as a diluent feed into the pyrolysis reactor, a feed stripping medium, as a fuel for the reactor, or as a byproduct. The light gases may contain a fraction of the methane separated from the remaining reactor product or cracked stock. Further, in some embodiments, the light gas separation may include additional stages or units to remove one or more of carbon dioxide ($CO_2$), hydrogen sulfide ($H_2S$), and water ($H_2O$), but also may include other reactive impurities. In particular, carbon dioxide and hydrogen sulfide, if present, may be removed by washing the stream with a solution of alkali or a salt of an amine or organoamine. If water is present, it may be removed by a methanol treatment, such as described in Belgian Patent No. 722,895. Other methods for removing water are adsorption and extraction by diethylene glycol. Various exemplary embodiments of this process are described further below.

Optionally, after block 210 and prior to block 214, a heavier product separation may conduct away a product of condensables from the remaining reactor product. The condensables may include vaporized liquids that condense, such as benzene, or are separated via cooled separations for example, adsorption, vapor liquid separators, flash drums etc. Certain exemplary embodiments of this process are described further below in FIGS. 3 and 4.

Figure 3:
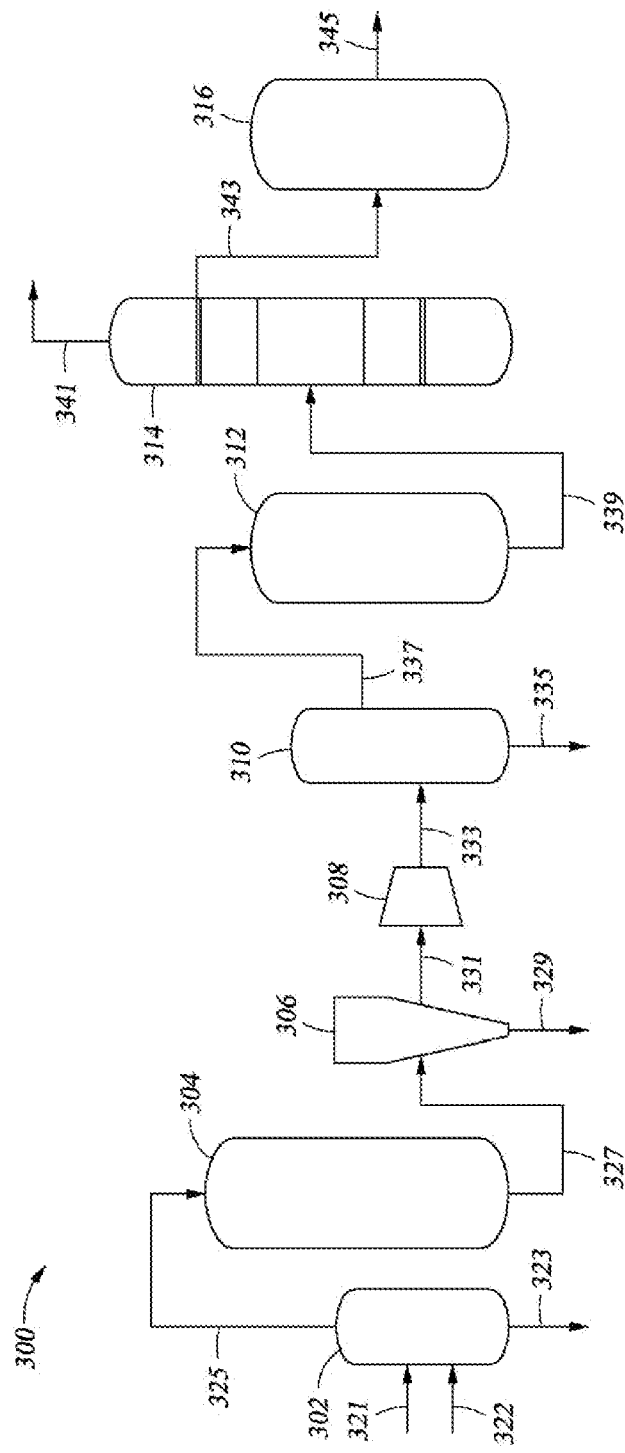
FIG. 3 is a simplified diagrammatic illustration of an exemplary process for converting hydrocarbon feed to polyethylene in accordance with an embodiment of the present techniques.

FIG. 3 is a simplified diagrammatic illustration 300 of an exemplary process for converting hydrocarbon feed to a polyethylene stream 345 in accordance with an embodiment of the present techniques. In this illustration 300, a particular configuration of unit operations (i.e. units) are coupled together to convert a hydrocarbon feed to polyethylene. These units may include a feed separation unit 302, a thermal pyrolysis reactor 304, solid removal unit 306, a compressor 308, a product separation unit 310, an acetylene converter 312, a purification unit 314 and an ethylene polymerization unit 316. In particular for this configuration, the feed preparation stage may include the feed separation unit 302, the cracking stage may include the thermal pyrolysis reactor 304, the recovery stage may include solid removal unit 306, a compressor 308, a product separation unit 310, an acetylene converter 312, a purification unit 314, and the polyethylene polymerization stage may include the ethylene polymerization unit 316. The process will now be explained in more detail.

A hydrocarbon feed, such as fuel oil (e.g., atmospheric resid) and/or natural gas, or other suitable hydrocarbon feed, is provided via line 321 to the feed separation unit 302. As noted above, the hydrocarbon feed may have a hydrogen content of 6 wt % to 25 wt %, 8 wt % to 20 wt % (e.g., not methane), or 20 wt % to 25 wt % (e.g., natural gas). Optionally, a diluent feed may be provided via line 322, which may include $H_2$, water or a lighter hydrocarbon, which lighter hydrocarbon is preferably a hydrocarbon with a high hydrogen content. The diluent feed may be used to adjust the hydrogen content of the hydrocarbon feed to form a pyrolysis feed having a hydrogen content above a certain threshold. The feed separation unit 302 may be used to separate the feed into a vapor product and a solid/liquid product. Examples of equipment suitable for separating the vapor product from the liquid product include a knockout drum (e.g., substantially any vapor-liquid separator), a flash drum, distillation column/unit, flash drum having a heating means within the drum, a knockout drum having heating means within the knock-out drum, and combinations thereof. During separation the temperature of the feed separation unit 302 is maintained between 50° C. and 750° C. or preferably between 100° C. and 515° C., which may be adjusted to control the separation level within the feed separation unit 302. Depending on the hydrocarbon feed, the vapor product may be readily separated from the remaining non-volatiles. Without separation, the solid/liquid product of the hydrocarbon feed may foul downstream lines or units. The liquid product, which may include non-volatiles, may be withdrawn or removed from the feed separation unit 302 as a bottoms product or stream via line 323, which may be further processed or utilized for fuel for the thermal pyrolysis reactor 304 or other units. The vapor product, which is the pyrolysis feed, may be withdrawn from feed separation unit 302 as an overhead stream via line 325 and passed to the thermal pyrolysis reactor 304. The pyrolysis feed may optionally be adjusted to have a hydrogen content within a predetermined range, as noted above.

The thermal pyrolysis reactor 304, as noted above, may include a regenerative reverse flow reactor or other suitable reactor. Accordingly, the thermal pyrolysis reactor 304 may have different piping configurations to provide combustion feed (e.g., fuel) and the pyrolysis feed separately, depending on the specific configuration.

The reactor effluent or reactor product from the thermal pyrolysis reactor 304 is conducted away via line 327 to the solid removal unit 306 and other recovery stage units. The solid removal unit 306 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting due to carbon deposit buildup. Adsorption and filtration are limited to handling small amounts of solids and may be problematic for larger amounts of solids. As a result, one or more of these techniques may be coupled together in series to provide the separation. The solid-liquid phase of the reactor product may be conducted away from solid removal unit 306 as a bottoms product, which may be a bottoms stream, via line 329. The bottoms product may include carbon black, soots, and/or heavy aromatic oils and/or tars. If the bottoms product is "dry", it may be handled via filtration or electrostatic separation; if sticky or wet, it may be better handled via washing (oil or water) or absorption. The bottoms product may be recycled to the thermal pyrolysis reactor or may be used as a fuel (in the reactor or process). The remaining portion of the reactor effluent or reactor product may be withdrawn from solid removal unit 306 as an overhead stream via line 331 and passed to the compressor 308.

The compressor 308 may receive the vapor product from the solid removal unit 306 and compress the product and provide the compressed product via 333 to the product separation unit 310. The compressor 308 may compress to the vapor product to a pressure from 50 psig to 400 psig, or more preferably from 150 psig to 300 psig. For other embodiments, the pressure may be adjusted for hydrogen ($H_2$) removal (e.g., pressure swing adsorption, hydrogen membrane and/or cryogenic distillation, electrochemical separation) and acetylene hydrogenation.

Once compressed, different products, such as different light gases or heavier products may be separated from the at least a portion of the reactor product in the product separation unit 310. The product separation unit 310 may include the different units discussed above along with caustic wash, amine scrubber and/or other treatments, which may also include steps to remove different products (e.g., $CO_2$, $H_2S$ and/or $H_2O$) from the process. For instance, carbon dioxide can be removed by washing the reactor product. This step may also include drying to remove entrained water. At least a portion of the reactor product may be recovered from the product separation unit 310 as via line 335 and passed to the acetylene converter 312, while the impurities may be withdrawn as products or bottom streams via line 337, which may be further processed for the different impurities.

Optionally, the acetylene converter 312 may receive the at least a portion of the reactor product (e.g., acetylene-rich product or $C_2U$ products comprising acetylene and ethylene) from the product separation unit 310. The acetylene converter (A/C) selectively hydrogenates the acetylene to ethylene without significantly hydrogenating the ethylene to ethane. The acetylene converter may operate at feed levels ranging from 0.5 to 15 mol % acetylene. The acetylene converter may operate at pressures from 32 psig (221 kPag) to 400 psig (2758 kPag), at inlet temperatures of 50° C. to 300° C. and may utilize catalyst comprising group VI or VIII catalysts. Conversion levels for the hydrotreater may range from 70 wt % to 100 wt % acetylene conversion and may have selectivity to ethylene from 70 wt % to as high as 98 wt % to ethylene. The acetylene converter 312 may include an optional finishing acetylene converter to convert remaining levels of acetylene at 100 wt % conversion of the acetylene. This finishing acetylene converter may be in fluid communication with one or more units, such as the acetylene converter 312 or other units downstream of the acetylene converter 312. The acetylene converter 312 may include a hydrogenation unit, and optionally may further include a compressor, stream recycle components, desorption unit and/or separation unit.

In one embodiment, a conversion product of ≥50 wt % of ethylene may be conducted away from the acetylene converter 312 to storage or for further processing. As an example, the conversion product may be passed to the purification unit 314 via line 339. The purification unit 314 may include a demethanator tower (to remove $H_2$, $CH_4$, $N_2$ and CO) and a $C_2$ splitter to remove ethane and upgrade ethylene to polymer grade ethylene. The purification unit 314 may also include $C_2$ or $C_3$ refrigeration train, compression and additional distillation towers. This purification unit 314 may separate the conversion product from the acetylene converter 312 into one or more products and an upgraded product, such as an ethylene stream. The one or more products, which are provided to line 341, may include different light gas products (e.g., hydrogen, carbon monoxide, nitrogen, methane, and the like) or heavier products (e.g., ethane and $C_{3+}$ streams). A portion of the recovered products may be recycled for processing again in the thermal pyrolysis reactor, such as methane and/or hydrogen. Further, if the upgraded product is an ethylene stream, it may be provided to the ethylene polymerization unit 316 via line 343.

The ethylene polymerization unit 316 may be a catalytic reactor, which may include a gas catalyst and/or a liquid catalyst. The process may involve a catalyst, solvent and the feed stream, as discussed above.

In some embodiments, a portion of the acetylene in the reactor product may optionally be combined with other process steps to form other products. In particular, the portion of the acetylene may be an intermediate product or precursor in a process within a chemical plant, in route to other preferred products, such as vinyl esters, ethylene, acetaldehyde, propanal, propanol, acrylic acid, and/or the like.

In one or more embodiments, the hydrocarbon feed may be separated into a pyrolysis feed and a bottom stream prior to being provided to the thermal pyrolysis reactor. That is, the non-combustible non-volatiles, such as metals and/or ash, may be managed by conducting away these products from the hydrocarbon feed prior to the thermal pyrolysis. As such, this configuration is able to receive advantaged feeds and process them in an efficient manner to produce olefins.

Figure 4:
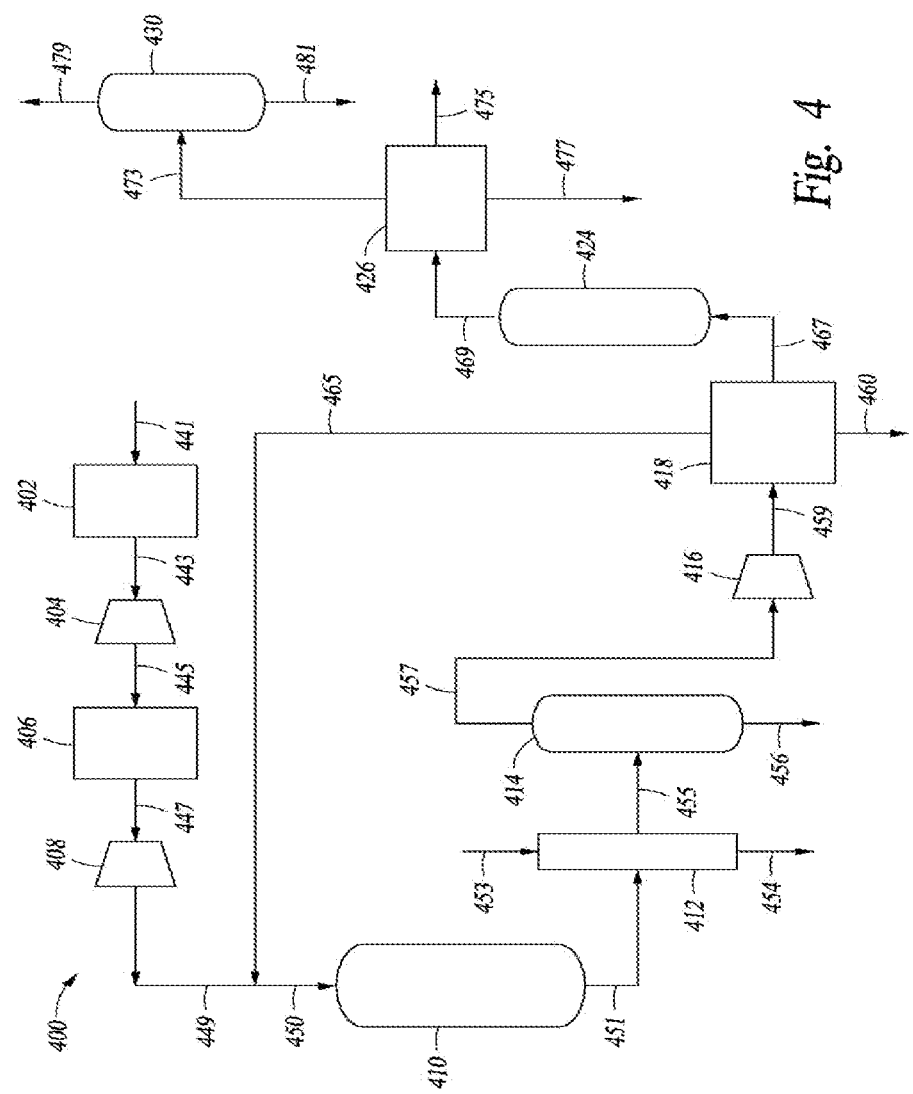
FIG. 4 is a simplified diagrammatic illustration of another exemplary process for converting hydrocarbon feed to polyethylene in accordance with an embodiment of the present techniques.

FIG. 4 is a simplified diagrammatic illustration of another exemplary process to convert a hydrocarbon feed, such as natural gas, to a final product, such as polyethylene, in accordance with an embodiment of the present techniques. In this illustration 400, a particular configuration of units are coupled together to convert hydrocarbon feed to a final product, such as polyethylene. In this configuration, the feed preparation stage may include an acid gas removal unit 402, a first expander 404, a recovery unit 406, a second expander 408, while the cracking stage may include the thermal pyrolysis reactor 410. The recovery stage may include a heat exchanger 412, a solid removal unit 414, a compressor 416, a product separation unit 418, an acetylene converter 424 and a purification unit 426. The polyethylene polymerization stage may include the ethylene polymerization unit (not shown). In addition, in this configuration, a power conversion stage is also provided, which may include a nitrogen splitter unit 430. Various piping may be utilized to couple these units together, as discussed below. Further, similar to the discussion related to FIGS. 2 and 3, various units in this configuration may operate and function in a substantially similar manner to the units noted above in FIGS. 2 and 3.

To begin, a hydrocarbon feed may be provided via line 441 to an acid gas removal unit 402. The hydrocarbon feed may be raw natural gas, for example. The acid gas removal unit 402 may be configured to separate $H_2S$ and/or $CO_2$ products along with other sulfur species products from the hydrocarbon feed. The products may be provided to storage or conducted away from the process for further processing (not shown).

Then, the feed or stream is provided from the acid gas removal unit 402 via line 443 to the first expander 404. The first expander 404 may be used to depressurize the stream. For example, the stream may be expanded from a first or initial pressure of the hydrocarbon feed from the well to the gas plant pressure (e.g., nominally ≥1000 pounds per square inch gauge (psig)) to the pressure utilized for natural gas liquid (NGL) separation (e.g., 200 psig). The expanded stream may be provided via line 445 to the recovery unit 406. The recovery unit 406 may be used to separate natural gas condensates or NGLs (e.g., $C_{3+}$) products from the stream. The products may be provided to storage or conducted away from the process for further processing (not shown). Again, the stream may be provided to an optional second expander 408 via line 447. The second expander 408 may further depressurize the stream from 200 psig to the thermal pyrolysis reactor pressure, which may include a range from 3 psig to 200 psig.

The expanded stream may then be provided to the thermal pyrolysis reactor 410 via lines 449 and 450. The expanded stream may be the pyrolysis feed or may be combined with a recycle stream 465 that includes methane, hydrogen or a combination thereof to form the pyrolysis feed. Similar to the discussion above, the thermal pyrolysis reactor 410 may include any of a variety of reactors, such as a regenerative reverse flow reactor. Once cracked, the reactor product or reactor effluent from the thermal pyrolysis reactor 410 may be further processed in the recovery stage. Initially, the reactor product from the reactor may be passed to the heat exchanger 412 via line 451. The heat exchanger 412 may cool the reactor product sufficiently for compression. That is, the heat exchanger 412 may cool the reactor product to a temperature in the range of 50° C. to 400° C. or more preferably from 100° C. to 250° C., and utilize the reactor product along with a utility fluid to recover heat for other processes. In certain embodiments, the heat exchanger 412 may use indirect heat transfer to cool the reactor product from the reactor and minimize the addition of contaminants. In this embodiment, the reactor product from the reactor may pass through the process side of a transfer line heat exchanger (TLE), while a utility fluid may be provided to the TLE via line 453 and exit the TLE via line 454. In this manner, the reactor product from the reactor is maintained separate from the utility fluid, which may include boiler feed water, the hydrocarbon feed, the pyrolysis feed or other suitable fluid. By utilizing this TLE, the process may enhance the energy efficiency of the process or facility.

The cooled reactor product may then be provided to solid removal unit 414, which may be similar to the solid removal unit 306 of FIG. 3, via line 455. In the solid removal unit 414, a bottom product comprising solids and/or tars may be separated from the cooled reactor product via one or more different mechanisms. For instance, in an oil wash unit, quench oil is mixed with at least a portion of the reactor product to remove solids from the reactor product. For a cyclone unit, at least a portion of the reactor product is introduced into the vessel and the bottoms product having solids flow to the bottom, while the remaining reactor product flows out another outlet. As may be appreciated, different combinations of these units may be coupled together in series to form the solid removal unit 414. From the solid removal unit 414, a bottoms product (e.g., bottoms stream) may be provided for further processing via line 456.

Then, the remaining reactor product may be further cooled, dried and provided to the compressor 416 via line 457. That is, a second heat exchanger or cooler may cool the remaining reactor product from the solid removal unit 414 to a temperature in the range of −50° C. to 100° C. The compressor 416, which may operate similar to the compressor 308 of FIG. 3, may be used to pressurize the stream to 50 psig to 400 psig, depending on the subsequent processing step.

The pressurized stream may then be provided via line 459 to the product separation unit 418. The product separation unit 418 may separate different products from the remaining reactor product, such as light gas products or heavier products, for example. These products may be conducted away as one or more light gas products that include components that are lighter than $C_2$ hydrocarbons, or one or more heavier products that include components that are heavier than $C_2$ hydrocarbons. Lighter than $C_2$ components may include hydrogen, methane and any combination thereof, while heavier than $C_2$ components may include $C_{3+}$ products such as methyl acetylene or benzene. These light gas products may be completely or only partially removed from the remaining reactor product in product separation unit 418. The one or more of the different light gas products, such as hydrogen or other gases, may be recycled via line 465 or may be utilized in other units (not shown). The recycle stream provided via line 456 may contain small amounts of acetylene and/or ethylene due to inefficiency of the separations. The acetylene-rich product that remains after separation may be passed via line 467 to the acetylene converter 424, which may operate similar to the acetylene converter 312 of FIG. 3. Separated heavier products (e.g., benzene) may be passed via line 460 for storage, for further processing in other units (not shown), or may be recycled to the thermal pyrolysis reactor 410 as pyrolysis feed or as combustion fuel.

The acetylene-rich product may be processed in the acetylene converter 424 to form a conversion product that is provided via line 469 to purification unit 426, which may operate similar to the purification unit 314 of FIG. 3. The purification unit 426 may include a demethanator tower (to remove hydrogen ($H_2$), methane ($CH_4$), nitrogen ($N_2$) and carbon monoxide (CO)), a $C_2$ splitter to remove ethane and purify ethylene to polymer grade ethylene, or a $C_2$ or $C_3$ refrigeration train, compression and additional distillation tower. The ethylene product, which may be provided from line 475, may be provided to the ethylene polymerization unit (not shown). However, in this configuration, the purification unit 426 may separate the conversion product into a fuel product, such as methane and lighter gases, provided via line 473 to nitrogen splitter unit 430 for power generation stage. As part of the power conversion stage, the optional nitrogen splitter unit 430 may separate a nitrogen product from the fuel product. From the optional nitrogen splitter unit 430, a nitrogen product may be provided via line 479 for storage or further processing, while the fuel product may be provided via line 481 to storage or for further use as fuel. Similarly, a heavier conversion product (e.g., saturated $C_2^+$ components, such as ethane and/or propane) may be separated in the purification unit 426, which may be provided via line 477 for storage or further processing. Optionally, the heavier conversion product may be utilized as a recycle stream, or to be mixed with the output line 481 of the nitrogen splitter unit 430 for storage or further processing.

As a specific example, the configuration may be utilized to convert raw natural gas into polyethylene. In this example configuration, the feed preparation stage may include an acid gas removal unit 402, a first expander 404, a recovery unit 406, a second expander 408, while the cracking stage may include the thermal pyrolysis reactor 410, which may be a regenerative reverse flow reactor. The recovery stage may include a heat exchanger 412, a solid removal unit 414, a compressor 416, a product separation unit 418, an acetylene converter 424, and a purification unit 426 (which may include a de-methanizer unit and an ethylene splitter unit). The polyethylene polymerization stage may include the ethylene polymerization unit (not shown). In addition, in this configuration, a power conversion stage maybe also provided, which includes a nitrogen splitter unit 430. Various piping may be utilized to couple these units together.

In this embodiment, a hydrocarbon feed, such as raw natural gas, may be processed with the flexibility to manage or remove various components at different stages in the process. That is, non methane components of the natural gas (e.g., impurities, such as natural gas liquid (NGL), ethane, LPG, $H_2S$, $CO_2$, $N_2$, and mercaptans) may be removed or managed in the process. For example, the NGL, ethane or liquefied petroleum gas (LPG) may be removed from the process to be sold as separate products. Alternatively, the NGL or mercaptans may be provided to the reactor and converted into acetylene or ethylene. Similarly, the other impurities, such as $H_2S$, $CO_2$, and $N_2$, may be separated as products prior to or after the thermal pyrolysis reactor. That is, unlike other processes, the present techniques utilize operating conditions and the thermal pyrolysis reactor to manage the impurities.

By providing this flexibility, the process may be integrated with a gas production facility at various locations because the thermal pyrolysis reactor and operating conditions provide enhancements for managing impurities. For instance, the acid gas removal unit 402, first expander 404, recovery unit 406, and second expander 408, may be units within a liquefied natural gas (LNG) facility or gas production facility. In this type of configuration, other products may be separated from the natural gas stream, while certain impurities may remain within the pyrolysis feed provided to the reactor because certain impurities are expensive to separate, such as nitrogen. Further still, in certain embodiments, the feed may be processed to remove certain products or streams, which may be used for fuel. The fuel product may be provided to storage or may be provided via recycle streams to the thermal pyrolysis reactor, to power generation units, or to other equipment within the gas production facility. As a specific example, the products from lines 456, 460 and 477 may be recycled to the thermal pyrolysis reactor 410 or gas production facility as feed and/or fuel. As such, the present techniques provide flexibility in coupling with other processes, such as a gas production facility (e.g., an LNG facility, gas plant or similar facility), which provide capital savings by reducing the units utilized to process raw gas feeds.

Although the units of FIGS. 3 and 4 are shown as respective single and separate units, each of these units can alternatively comprise a plurality of units. For example, a separation unit may include more than one knockout drums, separators, and/or flash drums. Accordingly, different embodiments may utilize different units in this manner. Further, some additional embodiments, which are discussed further below, may be utilized in these embodiments of FIGS. 2 and 4.

In certain embodiments, the thermal pyrolysis reactor may be operated at different pressures to further enhance the operation of the system. For example, in some embodiments, the pyrolysis of volatized hydrocarbons may occur at different pressures, such between 5 psia and 414 psia, 15 psia to 164 psia, or 30 psia to 150 psia. Pressures higher or lower than that disclosed above may be used, although they may be less efficient.

Each of the thermal pyrolysis reactors may be operated at different temperatures based on the specific operation and process variations. The different thermal pyrolysis reactors may include specific mechanisms and processes to heat the pyrolysis feed. Accordingly, each reactor may include different means for measuring the temperature of that specific process.

As a specific example for a thermal pyrolysis reactor, the pyrolysis stream is heated by a solid material, which is heated by a combustion reaction. Usually, the solid material forms the channels that the pyrolysis stream travels through. The combustion reaction of combustion feed that heats the solid material may heat via convective and/or radiative mechanisms. In these reactors, the highest temperatures are observed in the stream that is heating the solids (e.g., combustion stream). At any location, the solid material has a temperature that is lower than that of the combustion stream from which it receives heat, while the pyrolysis stream being heated by the solid material has a temperature that is lower than the solid material. The specific temperature of the combustion stream, pyrolysis stream or solid material depends on its location within the reactor and on the configuration and/or operation of the pyrolysis reactor.

In certain thermal pyrolysis reactors (e.g., steam cracking furnace configuration), the heating and the pyrolysis process occur simultaneously, for example, with a combusting stream on one side of partition (typically a wall or tubular) and the pyrolysis stream on the other side. Such reactors operate at or near steady state. The partition between the combustion feed and the pyrolysis feed has real physical dimensions and the temperature is not equal at every location. For example, on the combustion side, temperatures may be hottest near a flame region, and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the chemistry and heat transfer that takes place in the reactor. The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to the partition may be higher, and may, in some infinitesimal layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

In a thermal pyrolysis regenerative reactor system, the heating and pyrolysis occur in sequential steps. First, a heating step, usually a combustion reaction or combustion step, is used to heat the solid material. Second, a pyrolysis step is carried out that absorbs heat from the solid material to effect a chemical reaction. The solid material may be in fixed orientation or in moving orientation. If moving, the solid is typically moved from a heating region to a pyrolysis region. Moving-solid systems appear to be step-wise from the perspective of the moving solid, however the gas streams may be at a steady state in any absolute location, and temperatures are defined very much as discussed for thermal pyrolysis furnace-type reactors. When the solid material is in fixed orientation, a regenerative system may use valves to alternate introduction of pyrolysis and heating streams into the solid-containing region. The solid material may be designed to facilitate the process of heat addition and removal. Checker bricks, tiles and monoliths may be used as the solid materials within the reactor. Such materials form a network of passages that are used by the gases in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors are not at steady state. That is, at any given location, the temperature changes. However, these reactors may be in a periodic steady state, meaning that the same cycling of temperatures occurs over and over as the reactor oscillates between heating and pyrolysis.

In a reverse-flow regenerative system, a reversal occurs in the direction of transit of the gases through the region that contains the solid material, and this reversal occurs in between the heating and pyrolysis steps. In some embodiments, reversal occurs between every step, and in other embodiments reversal occurs in alternating step changes. Regardless, the flow reversal enables substantial heat exchange between the incoming gas of one step and the outgoing gas of the alternate step. This results in a reactor that has highest temperatures near the middle of the flow path, and relatively cool temperatures at both ends of the reactor.

In a regenerative pyrolysis system, peak pyrolysis gas temperature is determined as follows. The peak pyrolysis gas temperature typically is experienced by the gases at the beginning of the pyrolysis step, because the solid material is typically at its highest temperature at the beginning of the pyrolysis step. One skilled in the art will appreciate that temperatures immediately proximate to the solid material may be higher, and may, in some infinitesimal layer, actually approach the solid temperature. However, the pyrolysis temperature referred to herein should be considered a bulk gas temperature, which is a temperature that may be measured by a device (such as a thermocouple) that is not in contact with the solid material. For example, if the gas is traveling through channels in a checkerbrick, tile or honeycomb solid material, the bulk gas temperature could be taken as the average temperature over any channel cross-section, and the peak pyrolysis gas temperature as the highest cross-sectional-average temperature of the pyrolysis stream.

Thermal pyrolysis reactors may also be characterized in terms of the residence time of pyrolysis gases in the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. Additionally, the high-severity residence time is defined as the time that pyrolysis stream components are exposed to temperatures above the severity threshold. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present application, residence time (in either form) may be approximated using interpolation and extrapolation of discreet composition and temperature measurements, and/or using model-based estimations of temperature and composition, as is known in the art.

In addition to the operating pressure, the one or more embodiments may include the conversion of feedstocks into higher value hydrocarbons, such as acetylene, at different temperatures. These temperatures may include high pyrolysis temperature, which in the past has been a significant barrier to commercialization and efficiency. The high severity thermal pyrolysis reactor according to the present techniques is a higher temperature hydrocarbon pyrolysis reactor that operates at higher temperatures than steam cracking reactors used in commercial steam cracking operations. For example, naphtha steam cracking operations typically operate at furnace radiant coil outlet temperatures of ≤about 815° C., which corresponds to the peak pyrolysis gas temperature. However, in the present techniques, the high severity thermal pyrolysis reactor may operate at peak pyrolysis gas temperatures between 1200.0° C. and 2200.0° C., preferably between 1400.0° C. to 1900.0° C. or more preferably at least 1540.0° C. In particular, for reactors with an isothermal heat profile, the temperatures may be between 1450.0° C. and 1700.0° C., or between 1540.0° C. and 1650.0° C. For reactors with a Gaussian like heat profile, the peak pyrolysis gas temperatures may be between 1450.0° C. and 1900.0° C. or 1540.0° C. and 1800.0° C. In some reactions, it may even be still more preferable to expose the pyrolysis feed to heat using very short residence times, such as ≤0.1 second, to a temperature in excess of 1600.0° C. Pyrolysis reactions that benefit from reaction or conversion of methane that may be a part of the pyrolysis feed, typically involve peak pyrolysis gas temperatures in excess of 1400.0° C. for the methane to react or convert. An exemplary preferred process may pyrolyze the feed stream within the reactor, such as at peak pyrolysis gas temperatures of from 1540.0° C. to 2200.0° C., and more preferably from 1600.0° C. to 1800.0° C. Exemplary residence times preferably may be short, such as ≤0.5 second, ≤0.3 second and preferably ≤about 50 milliseconds or in the range of 0.5 seconds to 0.001 seconds. High severity residence times are preferably ≤0.05 seconds, and more preferably ≤0.02 seconds.

As described earlier, achieving any peak pyrolysis gas temperature involves the existence of a solid temperature that is heated to a higher temperature, and a combustion gas temperature that is a higher temperature than the solid temperature. In one or more embodiments of the present techniques, the maximum temperature of the solid elements in the thermal pyrolysis system (e.g., tubulars for furnaces or heat transfer solids for regenerative systems) is between about 5° C. and about 500° C. higher than the peak pyrolysis gas temperature. In a preferred embodiment, the maximum temperature of the solid elements in the thermal pyrolysis system is between 10° C. and 100° C. higher than the peak pyrolysis gas temperature. Reverse flow regenerative reactors may also include some amount of quenching by means of heat removal to the heat transfer solids. In reverse flow regenerative reactor embodiments of the present techniques, the pyrolysis gas may be cooled to a temperature between 100° C. and 1000° C. by means of heat removal to the heat transfer solids in the reactor, and more preferably cooled to a temperature between 300° C. and 550° C.

In one or more embodiments, the hydrocarbon feed may include different hydrocarbon mixtures thereof. For instance, the hydrocarbon feed may include methane, which may be part of a natural gas stream. This feed, including associated hydrocarbon and impurity gases, may be supplied into the reactor system. The supplied feed may be sweetened and/or dehydrated natural gas. Natural gas commonly includes various concentrations of associated gases, such as ethane and other alkanes, preferably in lesser concentrations than methane. The supplied natural gas may include impurities, such as hydrogen sulfide $H_2S$ and nitrogen. Certain embodiments may also serve to simultaneously convert some fraction of the associated higher hydrocarbons to acetylene. In other embodiments, the present techniques and compositions may be utilized with liquid feeds, such a vacuum gas oil (VGO) or naphthas. In one or more embodiments, the hydrocarbon vapor feed is advantageously pyrolyzed with an overall hydrogen content of the hydrocarbon feed in the reactor pyrolysis-stage is ≥10 wt %, preferably ≥12 wt %, and more preferably ≥15 wt %. Further, in other embodiments, the hydrocarbon feed may be a mixture of heavy hydrocarbon feed and methane, having aggregate hydrogen content ≥15 wt %. This adds the flexibility of controlling the $H_2$ byproduct. If $H_2$ is valued at a fuel/feed value, a lower H content feed may be used to maximize the chemical product value; or if $H_2$ is valued at chemical value (methane steam reforming value), higher H content feeds may be preferred (to meet chemical value $H_2$ demand). This also adds feed flexibility to crack liquids when gas prices are high (relative to crude) and gas when liquid prices are high relative to gas.

As example, U.S. Patent Ser. No. 61/226,499, which is incorporated by reference, describes a process and regenerative pyrolysis reactor utilized for pyrolyzing a resid-containing hydrocarbon feedstock. These process steps and/or pyrolysis reactor may be utilized in one or more of the embodiments described above. For instance, this process may include (a) feeding a resid-containing hydrocarbon feedstock to a thermal cracking unit; (b) thermally cracking at least 60 wt % of the resid having a boiling point of at least 565° C. in the hydrocarbon feedstock to form a vapor phase containing cracked hydrocarbons, based upon the total weight of the hydrocarbon feedstock having a boiling point of at least 565° C.; (c) separating the vapor phase from remaining non-volatiles; and (d) converting the separated vapor phase in a regenerative pyrolysis reactor system into a pyrolysis product. The process may have a thermal cracking unit that includes a visbreaker and the process further comprises feeding a gas selected from the group consisting of hydrogen, methane and combinations thereof to the visbreaking unit while thermally cracking the resid, may have a thermal cracking unit that includes a coker and the process comprises thermally cracking the resid in the coker; may include gas at a temperature between 600° C. and 850° C. when introduced into the visbreaker; may include a separated vapor phase that is essentially free of non-volatiles, wherein the separated vapor phase contains ≤2 ppmw metals, may include thermally cracking at least 70 wt % of the resid in the thermal cracking unit; may include feeding the vapor phase to a vapor/liquid separation unit; may include maintaining a temperature of the vapor phase during separation at a temperature between 200° C. to 750° C.; may include at least 75 wt % of the resid-containing hydrocarbon feedstock is vaporized and fed to the regenerative reactor system, based upon the total weight of the resid-containing hydrocarbon feedstock; or may include the vapor phase that is converted in the regenerative pyrolysis reactor system to form the pyrolysis product comprising $C_2$-$C_4$ unsaturated hydrocarbons. An apparatus for preparing a resid-containing hydrocarbon feedstock for conversion in a regenerative pyrolysis reactor may include (a) a thermal cracking unit for cracking at least a portion of resid having a boiling point of at least 565° C. in a resid-containing hydrocarbon feedstock; (b) a separation unit to separate a vapor phase containing cracked hydrocarbons from remaining non-volatiles; and (c) a regenerative pyrolysis reactor to convert the separated vapor phase hydrocarbons to a pyrolysis product. The apparatus may further include the thermal cracking unit having at least one of a visbreaking unit and a coker; may include a regenerative pyrolysis reactor comprising (i) a reaction region for converting the separated vapor phase to $C_2$-$C_4$ unsaturated hydrocarbons within the reaction region, and (ii) a quenching region to quench the $C_2$-$C_4$ unsaturated hydrocarbons; may include a reverse flow regenerative pyrolysis reactor system; the separator unit as at least one of a distillation column, a flash drum, or a knockout drum; may have (i) a first reactor having first and second ends and a first channel for conveying a first reactant from the first to the second end, and a second channel for conveying a second reactant from the first to the second end; and (ii) a second reactor having primary and secondary ends, wherein the first and second reactors are oriented in a series flow relationship with respect to each other; may have at least one of the first channel and the second channel are separated by a barrier that prevents at least a majority of a stoichiometrically reactable first reactant from reacting with the second reactant within the first reactor; may have the thermal cracking unit configured to crack at least 60 wt % of the resid based upon the total weight of the hydrocarbon feedstock having a boiling point of at least 565° C.

In other embodiments, the thermal pyrolysis reactor may be a regenerative reverse flow reactor or regenerative pyrolysis reactor. Regenerative pyrolysis reactors are well suited for processing volatized or volatizable feedstocks that are substantially free of non-volatile components, such as metals, and other residual or nonvolatizable components, which would otherwise lay down, ash, and/or build up in the reactor. Examples of such reactors may be found in U.S. Patent App. Pub. Nos. 2007/0144940 and 2008/0142409. These references, which are incorporated by reference, teach a regenerative bed reverse flow reactor wherein the location of the exothermic reaction is controlled. The regenerative reactor bed is regenerated by supplying a first reactant through a first channel to a first regenerative bed and a second reactant through a second channel in the first regenerative bed, combining first and second reactants in a gas mixer, and reacting to produce a heated reaction product which is passed through a second regenerative bed to transfer heat thereto. Other examples may be found in U.S. Patent App. Pub. No. 2009/0008292 and 2009/008292; U.S. Pat. No. 7,491,250 U.S. Patent App. Pub. No. 2009/008292; and U.S. Patent App. Ser. No. 61/349,464, which are each incorporated by reference.

As an example, U.S. patent Ser. No. 11/643,541 (U.S. Patent App. Pub. No. 2007/0191664), which is incorporated by reference, describes a process and high severity regenerative thermal pyrolysis reactor utilized to manufacture acetylene from a methane or hydrocarbon-containing feed. These process steps and/or pyrolysis reactor may be utilized in one or more of the embodiments described above. For instance, the process may include a reactor system that includes (i) a first (quenching) reactor comprising a first end and a second end, and (ii) a second reactor comprising a primary end and a secondary end, the first and second reactors oriented in a series relationship with respect to each other such that the secondary end of the second reactor is proximate the second end of the first reactor. The process may include a two-step process wherein heat is (1) added to the reactor media via in-situ combustion step; and (2) removed from the reactor media via in-situ endothermic pyrolysis step. The combustion step may involve passing a first and second combustion reactant (combustion feeds) separately but simultaneously through the first (quenching) reactor, by supplying a first reactant through a first channel in the first reactor and supplying at least a second reactant through a second channel in the first reactor, such that the first and second reactants are supplied to the first reactor from the first end of the first reactor. The combustion step may further involve combining the first and second reactants at the second end of the first reactor and reacting the combined reactants to produce a heated reaction product; passing the heated reaction product through the second reactor to transfer at least a portion of the heat from the reaction product to the second reactor, and recovering an exhaust gas from the second reactor. Preferably, the combining is enhanced by a reactant (combustion feed) mixer that mixes the reactants to facilitate substantially complete combustion/reaction at the desired location, with the mixer preferably located between the first and second reactors. Thereafter, the endothermic pyrolysis step, which may be carried out at a pressure between about 5 pounds per square inch absolute (psia) (35 kPa absolute (kPaa)) up to about 45 psia (310 kPaa), supplies methane or other hydrocarbon through the heated second reactor to the first reactor, in flow direction the opposite to that of the heating (combustion) step, to convert at least a portion of the methane into acetylene; passing the supplied methane and the produced acetylene through the first reactor to quench the methane and the produced acetylene; and recovering the produced acetylene. The process may further include supplying hydrogen in the second reactor during the pyrolysis step to moderate the reaction of the methane or other hydrocarbons in the feed. Hydrogen may be used in molar ratio to methane of 0 to 5, preferably of 1 to 3 during the pyrolysis step. In a preferred embodiment, the media in the first reactor includes one or more honeycomb monolith structures that provide flow channels for the first and second reactant. The process may further include media of the first or second reactor that has wetted surface area between 50 and 3000 ft$^{-1}$, heat transfer coefficient $\geq 0.02$ cal/cm$^3$s° C., and bulk heat capacity $\geq$about 0.10 cal/cm$^{3\circ}$ C., and may be comprised of honeycomb monoliths having 40% to 80% open frontal area and between about 50 and 2000 channels per square inch. The process may further include compressors, blowers, or fans to supply air as one combustion feed during the combustion step, which may be carried out at a pressure between about 15 psia (103 kPaa) and 45 psia (310 kPaa); may include expansion turbines to recover mechanical energy from higher pressure exhaust gases; and may include recycle of exhaust gases (EGR) to the combustion feed for combination with the air, for example to reduce the oxygen content and the adiabatic flame temperature of the combustion feed. Non-combustible gases, for example, $H_2O$, $CO_2$ and $N_2$, may be added to the combustion feed to reduce combustion temperature. The combustion step may comprise a first and second reactant that are a fuel gas and an oxidant that are maintained substantially separated as they pass through the first reactor and which combust or burn when combined. By substantially separated is meant that at least 50%, and more preferably 75% or 90% of the potential combustion that may occur after the axial transit of the first reactor. The process may further include a mixer that is comprised of multiple mixer segments, each preferably having similar cross-sectional area and length and each preferably accepting flow during the combustion step from roughly equal numbers of first and second channels, representing roughly equal proportions of first and second reactant, and having a characteristic L/D between 0.1 and 5.0. Preferably, the mixer has a total volume $\leq 20\%$ of the total volume of mixer plus flow regions in first and second reactor, and preferably has a geometric void volume $\leq 20\%$ of the void volume in mixer plus first and second reactor. The process may further include a cycle time that includes the time spent in combustion step plus time spent in pyrolysis step plus any time needed to switch between steps. Typical cycle times may be between 1 and 240 seconds, or between 2 and 60 seconds, and without expectation that combustion and pyrolysis steps have equal durations.

As an example, U.S. patent Ser. No. 12/119,762, which is incorporated by reference, describes a process and regenerative pyrolysis reactor utilized for pyrolyzing a hydrocarbon feedstock containing non-volatiles. These process steps and/or pyrolysis reactor may be utilized in one or more of the embodiments described above. For instance, the process may include heating the non-volatile-containing hydrocarbon feedstock to a temperature sufficient to form a vapor phase that is essentially free of non-volatiles and a liquid phase containing non-volatiles; separating the vapor phase from the liquid phase; feeding the separated vapor phase to the regenerative pyrolysis reactor system; and converting the separated vapor phase in the regenerative pyrolysis reactor system to form a pyrolysis product. Further, the process may include quenching the converted separated vapor phase to form the pyrolysis product; may include heating the non-volatile-containing hydrocarbon feedstock to a temperature in the range of from about 200° C. to about 650° C.; may include feeding at least one of a diluent and a stripping agent to the pyrolysis reactor system while transferring the at least a portion of the separated vapor phase to the pyrolysis reactor system for cracking the vapor phase in the presence of the at least one of the diluent and the stripping agent within the pyrolysis reactor system, wherein the at least one of the diluent and the stripping agent comprises at least one of hydrogen and steam; may include heating of the hydrocarbon feedstock via at least one of a heat exchanger, steam injection, and a fired heater.

As another example, U.S. patent Ser. No. 12/121,353, which is incorporated by reference, describes a process and regenerative pyrolysis reactor utilized for pyrolyzing a hydrocarbon feedstock containing non-volatiles. These process steps and/or pyrolysis reactor may be utilized in one or more of the embodiments described above. For instance, this process heating the non-volatile-containing hydrocarbon feedstock upstream of a regenerative pyrolysis reactor system to a temperature sufficient to form a vapor phase and a non-volatile-containing liquid phase; separating the vapor phase from the liquid phase; feeding the separated vapor phase and methane to the regenerative pyrolysis reactor system; and converting the separated vapor phase in the regenerative pyrolysis reactor system to form a pyrolysis product. The process may further include the separated vapor phase that is substantially free of non-volatiles; may include quenching the converted separated vapor phase to form the pyrolysis product; or may heat non-volatile-containing hydrocarbon feedstock to a temperature in the range of from about 200° C. to about 650° C. The heating of the hydrocarbon feedstock may be carried out by at least one of a heat exchanger, steam injection, the reactor system, a fired heater, and combinations thereof upstream of a regenerative pyrolysis reactor system.

As another example, U.S. Patent Ser. No. 61/349,464, which is incorporated by reference, describes a process and regenerative pyrolysis reactor utilized for pyrolyzing a hydrocarbon feedstock. These process steps and/or pyrolysis reactor may be utilized in one or more of the embodiments described above. For instance, a reactor may include a reactor body, wherein the reactor body forms a reaction region within the reactor body; a packing material disposed at least partially within the reaction region; and one or more poppet valve assemblies coupled to the reactor body and in flow communication with the reaction region and controlling fluid flow between a location external to the reactor body and within the reaction region. Further, a reactor may include a reactor body; a first head engaged with the reactor body; a first conduit extending from outside the head to at least partially through the head; and a first valve in flow communication with the first conduit controlling fluid flow along a flow path extending from the first valve and through the reactor body. The reactor may further include a second head engaged with the reactor body; a second conduit extending from outside the first head or the second head to at least partially through the respective head; and a second valve in flow communication with the second conduit controlling fluid flow along the flow path including a portion extended from the reactor body to the second valve; may be configured wherein the first valve has a substantially open position when fluid flow in the flow path is in a first flow direction and a substantially closed position when fluid flow in the flow path is in a second, opposite flow direction; may have a first valve pair on opposite sides of at least a portion of the flow path, wherein the first valve and second valve are each in a substantially open position when fluid flow in the flow path is in a first flow direction and a substantially closed position when fluid flow in the flow path is in a second, opposite flow direction; may include a third conduit extending from outside the first head or the second head to at least partially through the respective head; a third valve in flow communication with the third conduit controlling fluid flow along the flow path including a portion extended from the reactor body to the third valve; a fourth conduit extending from outside the first head or the second head to at least partially through the respective head; and a fourth valve in flow communication with the second conduit controlling fluid flow along the flow path including a portion extended from the reactor body to the fourth valve; and may have a second valve pair comprising the third valve and the fourth valve on opposite sides of at least a portion of the flow path, controlling flow in the second, opposite flow direction wherein the third valve and the fourth valve are each in a substantially closed position when the fluid flow in the flow path is in the first flow direction and in a substantially open position when fluid flow in the flow path is in the second, opposite flow direction; may include one or more additional valves, each in flow communication with one of the first, second, third, or fourth conduits via an additional conduit extending at least partially through the additional conduit's respective head, operating in phase with any other valves in fluid communication with the additional conduit and controlling fluid flow along the flow path including a portion extended from the reactor body to the respective valve; may include a reactor bed, and the volume of the flow path consists of (i) a packed flow path volume within a solids-fluids contact portion of the reactor bed and (ii) an open flow path volume between the valve(s) and the reactor bed, as well as any open flow portion within the reactor bed; may have a packed flow volume comprising all volume in the reactor bed that is at a distance ≤2 cm from a solids-fluid contact surface; may have a solids-fluids contact portion of the reactor bed having a wetted area ≥0.5 $cm^2/cm^3$ in all regions of the portion of the reactor bed; may have a ratio of the open flow path volume to packed flow path volume is ≤1; may have a ratio of the open flow path volume to packed flow path volume is ≤0.5; may include a reactor bed that has a fixed bed core comprising solid material capable of heat exchange; may include at least one of the valves is a poppet valve comprising a disk element connected to a valve stem element; may have a distance during operation between the poppet valve disk element flat surface in the fully open position and the reactor bed surface is between 5% and 200% of the disk element diameter; may have a distance during operation between the poppet valve disk element flat surface in the fully open position and the reactor bed surface is between 20% and 80% of the disk element diameter, may extend the poppet valve stem element to a location outside the head; may have each valve associated with an externally accessible valve seat that fits within its respective inlet to the reactor body and/or outlet from the reactor body and is sealed to the head, wherein the valve seat is attached to the head via one of a rotatable locking mechanism, thread-in seats, and pressed-in seats; may include a valve stem seal associated with the valve stem; may include a valve stem seal that is a reciprocating compressor-type seal, may include an actuator that is at least one of pneumatically actuated, hydraulically actuated, and electromagnetically actuated.

In other embodiments, the use of a reverse flow regenerative reactor in the process may be utilized to remove other inefficiencies. That is, while certain embodiments may include heat exchangers for heat recovery, the quenching step is performed within the reactor as part of the process, not as a separate step. For instance, certain embodiments may avoid an active quench stage, as the reactor product from the reverse flow regenerative reactor is cooled passively prior to exiting the reactor. That is, an expensive water or oil quench tower for rapid temperature reduction may not be utilized with the different configurations above. Active quench systems include a separate unit or step outside the reactor, such as mixing water or oil with the stream, or expanding in a kinetic energy quench, such as a Joule Thompson expander, choke nozzle, or turbo expander. Unlike the active quench stage, the present techniques utilize the flow through the reactor to cool the reactor product. In this manner, the inefficiencies of a quench step are removed from this process because the effluent is passively quenched by flow within the reactor.

In one or more embodiments, heat recovery may be utilized within the system to further enhance the operation. For example, the outlet temperatures may be below 600° C., below 500° C., or in a range from about 200° C. to about 600° C., or more preferably from about 300° C. to about 500° C. Accordingly, heat exchangers, such as TLEs, may be used to recover heat between units or process steps.

Further, other embodiment may include a dilute acetylene stream, which may be compressed with inter-stage cooling and drying as appropriate for a secondary conversion stage. The products are washed (caustic wash or amine scrubbing) to remove acidic species and impurities as necessary for the production of high purity polyolefin feed. The dilute acetylene is hydrogenated in an acetylene converter to yield dilute ethylene (advantageously, without the addition of a separate $H_2$ stream). The dilute ethylene is purified and traces of methane, ethane, residual acetylenes and CO are removed and the resulting high purity ethylene (polymer grade) is polymerized to polyethylene in a separate reactor.

In some other embodiments, the use of the materials may provide additional benefits in the selectivity of operations. For example, regenerative pyrolysis reactors generally have not been used commercially to temperatures above 1300° C. because of the alumina internals and the process, as noted in the references discussed above. In a regenerative reactor, which utilizes the materials noted herein, the operating temperatures within the reactor may reach temperatures up to 1500° C. to 2200° C. In this manner, the process may be operated at a higher conversion, at high selectivity and reduce the overall capital cost of the process. That is, the process may produce fewer byproducts by operating at these higher temperatures.

Further, the temperature within the pyrolysis reactor may also involve large swings in temperatures. Accordingly, pyrolysis reactors materials have to be designed to withstand these temperature swings. That is, in the proposed configuration, pyrolysis reactors may have components or internals, such as valves, tubes, conductive monoliths, thin-walled honeycombs, bead-beds, mixers, quench media, and other reactor components, regardless of whether simple or complex shaped, that are directly associated with the pyrolysis reaction. These components are made of different materials able to withstand these larger temperature swings. As a specific example, a regenerative reverse flow reactor may include different materials for its internal components. That is, the components may be substantially formed from, predominately formed from or partially formed from certain materials, such as refractory materials (some of which are noted below). For instance, a regenerative reverse flow reactor may include a first reactor and a second reactor in flow communication with the first reactor, the first reactor comprising a first channel for conveying a first reactant through the first reactor to the second reactor and a second channel for conveying a second reactant through the first reactor to the second reactor, the first reactant exothermically reacting with the second reactant in the second reactor. Further, the reactor may include components, such as a honeycomb monolith, a reactor bed, a reactor conduit, and a reactant mixer, which is made completely from one of the materials, discussed or is made substantially from one or more of the materials. Certain of these components may have flow channels to provide passage for fluids through the components, such as a honeycomb monolith.

As an example, the reactor component, such as a monolith, may be made from (e.g., substantially, predominately or partially made from) a refractory material in oxide form, wherein the refractory material has a melting point of no less than 2060° C. and which remains in oxide form for at least one of: (i) when exposed to a gas having an oxygen partial pressure of $10^{-15}$ bar, a carbon partial pressure above the carbon partial pressure of the zirconium carbide and zirconium oxide phase transition at the same temperature, and at temperatures below the temperature of the zirconium triple point at the oxygen partial pressure of $10^{-15}$ bar; and (ii) when exposed to a gas having an oxygen partial pressure of $10^{-15}$ bar and at temperatures above the zirconium triple point at the oxygen partial pressure of $10^{-15}$ bar.

As another example, U.S. patent Ser. No. 12/099,251, which is incorporated by reference, describes a pyrolysis reactor having components or internals, which are exposed to heat within the reactor region, formed from materials made of stabilized zirconia. These components or internals may be utilized in one or more of the embodiments described above. In particular, the components may be formed for, a stabilized refractory grade zirconia, which has a thermal shock resistance rating that demonstrates a total crack length per unit area after quenching the stabilized refractory grade zirconia from 1100° C. into a water bath to a temperature of 50° C. is not greater than 30 cm/cm$^2$ or not greater than 5 cm/cm$^2$; may have a modulus of rupture mechanical flexural strength of not less than 13.8 MPa prior to initially heating the stabilized refractory grade zirconia to 1000° C.; may have a modulus of rupture mechanical flexural strength of not less than 13.8 MPa when heated to a temperature in a range of from 1000° C. to 1800° C. or to 2000° C.; may have a modulus of rupture mechanical flexural strength measured at 50° C. after quenching from a temperature in a range of from 1000° C. to 1800° C. that is at least 70% of the stabilized refractory grade zirconia's modulus of rupture mechanical flexural strength measured at a temperature in a range of from 1000° C. to 1800° C.; may have a modulus of rupture mechanical flexural strength measured at 50° C. after quenching from a temperature in a range of from 1000° C. to 1800° C. that is at least 80% of the stabilized refractory grade zirconia's modulus of rupture mechanical flexural strength measured at a temperature in a range of from 1000° C. to 1800° C. Further, the stabilized refractory grade zirconia may be stabilized by at least one stabilization component comprising at least one of CaO, MgO, $Y_2O_3$, $CeO_2$, and mixtures thereof; may include at least 1.0 wt % of the stabilization component, based upon the total weight of the stabilized refractory grade zirconia; may include from 0.001% to 10% by weight, based upon the weight of the stabilized refractory grade zirconia, of secondary oxides that comprise elements selected from the group consisting of Al, Si, Mg, Ca, Y Fe, Mn, Ni, Co, Cr, Ti, Hf, V, Nb, Ta, Mo, W, Sc, La, and Ce, and mixtures thereof. The stabilized refractory grade zirconia may include a partially stabilized refractory grade zirconia; may include the partially stabilized refractory grade zirconia that includes a thermal shock resistance rating that demonstrates a total crack length per unit area after quenching the partially stabilized refractory grade zirconia from 1100° C. into a water bath to a temperature of 50° C. is not greater than 5 cm/cm$^2$; may have a modulus of rupture mechanical flexural strength of not less than 27.6 MPa when heated to a temperature in a range of from 1000° C. to 1800° C.; may have a modulus of rupture mechanical flexural strength measured at 50° C. after quenching from a temperature in a range of from 1000° C. to 1800° C. that is at least 80% of the partially stabilized refractory grade zirconia's modulus of rupture mechanical flexural strength measured at a temperature in a range of from 1000° C. to 1800° C.; and may be stabilized by at least one stabilization component comprising at least one of CaO, MgO, $Y_2O_3$, $CeO_2$, and mixtures thereof.

As yet another, U.S. patent Ser. No. 12/277,056, which is incorporated by reference, describes a pyrolysis reactor having components or internals, which are exposed to heat within the reactor region, formed from a ceramic material. These components or internals may be utilized in one or more of the embodiments described above. The ceramic component may include a multimodal grain distribution including: (i) at least 50 wt % of coarse grains including stabilized zirconia, the coarse grains comprising a D50 grain size in the range of from 5 μm to 800 μm, based upon the total weight of the component; and (ii) at least 1 wt % of fine grains comprising a D50 average grain size not greater than one-fourth the D50 grain size of the coarse grain, dispersed within the coarse grains, based upon the total weight of the component; wherein after sintering, the component has porosity at an ambient temperature in the range of from 5 vol. % to 45 vol. %, based on the volume of the formed component. The component may have fine grains that include at least one of (i) a stabilized zirconia, (ii) a stabilizer, and (iii) mixtures thereof, wherein the stabilizer may include $Y_2O_3$; may have a flexural strength (MOR) of at least 6 kpsi and a normalized thermal shock resistance rating of at least four; was sintered at a temperature of at least 1500° C.; may have a flexural strength (MOR) of at least 6 kpsi and a normalized thermal shock resistance rating of at least four; may have a flexural strength is at least 10 kpsi; may have the fine grain mode that comprises a D50 grain size of from 0.01 μm to 100 μm; may have the fine grain mode that includes a D50 grain size of 0.05 μm to 44 μm; may have the fine grain mode that comprises a D50 grain size of from 0.05 μm to 5.0 μm, and the coarse grain mode comprises a D50 grain size of from 20 μm to 200 μm; may have a fine grain mode that includes a D50 grain size that is not greater than one-eighth the size of a D50 average grain size of the coarse grain mode; may have a bimodal distribution of grains comprises from 1 wt % to 20 wt % of the fine grains and from 80 wt % to 99 wt % of the coarse grains; may have a bimodal distribution of grains comprises from 1 wt % to 15 wt % of the fine grains and from 85 wt % to 99 wt % of the coarse grains; may have a sintered component after annealing at a temperature of at least 1800° C. for two hours the component includes porosity at ambient temperature in the range of from 5 vol % to 45 vol % based upon the volume of the component, a MOR of at least 6 kpsi, and a normalized thermal shock resistance rating of at least four; may have a flexural strength (MOR) of at least 6 kpsi and a normalized thermal shock resistance rating of at least four; may have a porosity in the range of from 10 vol % to 30 vol % based on the volume of the formed component; may be formed of coarse grain stabilized zirconia and is stabilized by at least 1 wt % of a stabilizer that includes at least one of CaO, MgO, $Y_2O_3$, $CeO_2$, and mixtures thereof, based upon the weight of the coarse grain stabilized zirconia; may have from 0.001 wt % percent to 10 wt %, based upon the weight of the component, of an oxide that comprises elements selected from the group consisting of Al, Si, Mg, Ca, Y Fe, Mn, Ni, Co, Cr, Ti, Hf, V, Nb, Ta, Mo, W, Sc, La, Ce, and mixtures thereof, which the oxide may include from 0.01 to 5.0 wt % of the component, based on the total weight of the component; may have a shape of at least a majority by weight of the coarse grains have a shape factor of not greater than 2.5; may have the shape of at least a majority by weight of the fine grains have a shape factor of not greater than 2.5; or may have the multimodal grain distribution further includes (iii) at least 5 wt % of an intermediate grain mode of stabilized zirconia including a D50 grain size intermediate the D50 grain size of each of the coarse grain mode and the fine grain mode, based upon the total weight of the component.

Further, in other embodiments, a multimodal ceramic component may include at least a fine grain mode and a coarse grain mode, the coarse grain mode comprising stabilized zirconia and the fine grain mode comprising at least one of stabilized zirconia and stabilizer; wherein after sintering, the component includes porosity at ambient temperature in the range of 5 vol % to 45 vol %, based on the volume of the ceramic component. The multimodal ceramic component may have a flexural strength of at least 6 kpsi along with a normalized thermal shock resistance rating of at least four; have (i) at least 50 wt % of the coarse grain mode including stabilized zirconia, the coarse grain mode including a D50 grain size in the size range of from 5 μm to 800 μm, based upon the total weight of the component; and (ii) at least 1 wt % of the fine grain mode including at least one of stabilized zirconia and a metal oxide stabilizer, the fine grain mode including a D50 grain size in the range of 0.01 μm to 100 μm dispersed within the coarse grain mode, based upon the total weight of the component; having the stabilized zirconia is stabilized by at least 1 wt % of a stabilizer that includes at least one of CaO, MgO, $Y_2O_3$, $CeO_2$, and mixtures thereof, based upon the weight of the coarse grain stabilized zirconia; has from 0.001 wt % to 10 wt %, based upon the weight of the component, of oxides that comprise elements selected from the group consisting of Al, Si, Mg, Ca, Y Fe, Mn, Ni, Co, Cr, Ti, Hf, V, Nb, Ta, Mo, W, Sc, La, Ce, and mixtures thereof; has a coarse grain mode stabilized zirconia comprises partially stabilized zirconia; and has a stabilized zirconia of the fine grain mode comprises fully stabilized zirconia.

For example, U.S. patent Ser. No. 12/277,056, which is incorporated by reference, describes a pyrolysis reactor having components or internals, which are exposed to heat within the reactor region, formed from refractory materials. These components or internals may be utilized in one or more of the embodiments described above. In particular, the refractory material may include (i) at least 20 wt % of a first grain mode based upon the total weight of the refractory material, the first grain mode comprising stabilized zirconia having a D50 grain size in the range of from 5 μm to 2000 μm, the stabilized zirconia including a matrix oxide stabilizer; (ii) at least 1 wt % of a second grain mode having a D50 grain size in the range of from 0.01 μm up to not greater than one-fourth the D50 grain size of the first grain mode zirconia, based upon the total weight of the refractory material; and (iii) the refractory material comprising at least 1 wt % of a preservative component; wherein after sintering the material has porosity at 20° C. of from 5 vol % to 45 vol %. Further, the material may have a preservative component provided within one or more of (a) the first grain mode, (b) the second grain mode, and (c) an optional grain mode, and the at least 1 wt % that is determined by the aggregate of preservative component within the refractory material; may include at least 10 wt % of combined weight of the preservative component, the matrix oxide stabilizer, and optionally a second grain mode zirconia stabilizer, based upon the total weight of the refractory material; may have an aggregate weight of the matrix oxide stabilizer, the preservative component, and an optional second grain mode zirconia stabilizer comprises at least 10 wt % of the material, based upon the total weight of the material; may have a ceramic component that comprises a flexural strength (MOR) of at least 6 kpsi and a normalized thermal shock resistance rating of at least four; may have the first grain mode that comprises stabilized zirconia having a D50 grain size in the range of from 5 μm to 800 μm; may have the first grain mode stabilized zirconia comprises at least 6 wt % of matrix oxide stabilizer, the matrix oxide stabilizer comprising at least one of an yttrium-containing compound, CaO, MgO, $Y_2O_3$, $CeO_2$, and mixtures thereof, based upon the weight of the first grain stabilized zirconia; may have the preservative component comprise at least one of an yttrium-containing compound, CaO, MgO, $Y_2O_3$, $CeO_2$, and mixtures thereof; may include (i) 20 wt % to 50 wt % of the first grain mode, based upon the total weight of the material; (ii) 1 wt % to 80 wt % of the second grain mode, based upon the total weight of the material; and (iii) a combined total of at least 1 wt % of the preservative component within at least one of the first grain mode, the second grain mode, and the optional another grain mode. The second grain mode may include a fully stabilized zirconia, the fully stabilized zirconia that is stabilized by at least 14 wt % of a second grain mode zirconia stabilizer based upon the weight of the second grain mode fully stabilized zirconia; may include the preservative component and a stabilized zirconia; and each of the preservative component and the second grain mode zirconia stabilizer comprises substantially the same compounds as comprise the first grain matrix oxide stabilizer; may include a fully stabilized zirconia, the second grain fully stabilized zirconia is stabilized by a second grain mode zirconia stabilizer; and may consists essentially of the preservative component; and may include at least 14 wt % of at least one of an yttrium-containing compound, CaO, MgO, $Y_2O_3$, $CeO_2$, and mixtures thereof, based upon the weight of the second grain mode.

As yet another example, U.S. patent Ser. No. 12/467,832, which is incorporated by reference, describes a pyrolysis reactor having components or internals, which are exposed to heat within the reactor region, formed from refractory material that includes an yttria stabilized zirconia. These components or internals may be utilized in one or more of the embodiments described above. The refractory material comprises at least 21 wt % yttria based upon the total weight of the refractory material. In particular, the material may have a porosity at 20° C. in the range of from 5 vol. % to 28 vol. % based upon the volume of the refractory material; may include at least 25 wt % yttria based upon the total weight of the refractory material; may have a porosity at 20° C. in the range of from 5 vol. % to 25 vol. % based upon the volume of the refractory material; may include at least a first grain mode including yttria stabilized zirconia and a second grain mode comprising yttria; may include (i) at least 20 wt % of a first grain mode based upon the total weight of the refractory material, the first grain mode comprising yttria stabilized zirconia having a D50 grain size in the range of from 5 μm to 2000 μm, the first grain mode comprising at least 6 wt % yttria based upon the weight of the first grain mode, and (ii) at least 1 wt % of second grain mode based upon the total weight of the refractory material, the second grain mode having a D50 grain size in the range of from 0.01 μm up to not greater than one-fourth the D50 grain size of the first grain mode stabilized zirconia, the second grain mode comprising at least 14 wt % yttria based upon the weight of the second grain mode; may include at least one of yttria oxide, an yttrium containing compound, and combinations thereof; may include the refractory material comprises yttria and/or yttria stabilized zirconia, at least one of the yttria and/or the yttria stabilized zirconia having a D50 grain size in the range of from 0.01 μm to 2000 μm; may include at least 30 wt % yttria based upon the total weight of the refractory material; may have a porosity at 20° C. in the range of from 10 vol. % to 20 vol. % based upon the volume of the refractory material; may have from 0.001 wt % to 5 wt % based upon the weight of the refractory material, of compounds that comprise elements selected from the group consisting of Al, Si, Mg, Ca, Fe, Mn, Ni, Co, Cr, Ti, Hf, V, Nb, Ta, Mo, W, Sc, La, and Ce, and mixtures thereof. The first grain mode may include at least 14 wt % yttria based upon the weight of the first grain mode; or may include stabilized zirconia having a D50 grain size in the range of from 5 μm to 800 μm. The second grain mode comprises yttria fully stabilized zirconia; may consists essentially of yttria; may include at least 50 wt % of yttria fully stabilized zirconia comprising at least 14 wt % yttria, based upon the weight of the first grain mode; may include yttria fully stabilized zirconia, and excess the yttria is included within one or more of (a) the first grain mode, (b) the second grain mode, and (c) an optional another grain mode.

As still yet another example, U.S. patent Ser. No. 12/772,757, which is incorporated by reference, describes a pyrolysis reactor having components or internals, which are exposed to heat within the reactor region, which formed from refractory material in oxide form. These components or internals may be utilized in one or more of the embodiments described above. The refractory material has a melting point of no less than 2060° C. and which remains in oxide form for at least one of: (i) when exposed to a gas having an oxygen partial pressure of $10^{-15}$ bar, a carbon partial pressure above the carbon partial pressure of the zirconium carbide and zirconium oxide phase transition at the same temperature, and at temperatures below the temperature of the zirconium triple point at the oxygen partial pressure of $10^{-15}$ bar; and (ii) when exposed to a gas having an oxygen partial pressure of $10^{-15}$ bar and at temperatures above the zirconium triple point at the oxygen partial pressure of $10^{-15}$ bar. The refractory material may remain in oxide form when exposed to a gas having an oxygen partial pressure of $10^{-15}$ bar, a carbon partial pressure above the carbon partial pressure of the zirconium carbide and zirconium phase transition at the same temperature, and at temperatures above the zirconium triple point at the oxygen partial pressure of $10^{-15}$ bar; may remain in oxide form when exposed to a gas having carbon partial pressure of $10^{-11}$ bar, an oxygen partial pressure of $10^{-15}$ bar, at a temperature of 2050° C.; may have a melting point of no less than 2160° C.; may remain in the oxide form when exposed to a reference pyrolysis gas mixture having a carbon partial pressure of $10^{-10}$ bar, an oxygen partial pressure of $10^{-15}$ bar, and at a temperature over the full range of from 1800° C. to 2100° C.; may have a crystalline structure that is cubic during heat-up from 1250° C. to 2250° C.; may have a vapor pressure of the refractory material is $\leq 10^{-7}$ bar at 2000° C.; may have at least a first grain mode comprising yttria and a second grain mode comprising yttria; may substantially exclude oxides of toxic ceramics; may include at least one of yttria, another yttrium containing compound, a zirconium containing compound, and combinations thereof; may include from 0.001 wt % to 5 wt % based upon the weight of the refractory material, of compounds that comprise elements selected from the group consisting of Al, Si, Mg, Ca, Fe, Mn, Ni, Co, Cr, Ti, Hf, V, Nb, Ta, Mo, W, Sc, La, and Ce, and mixtures thereof.

Further still, another example, U.S. patent Ser. No. 12/623,046, which is incorporated by reference, describes a pyrolysis reactor having components or internals, which are exposed to heat within the reactor region, which formed from refractory material in oxide form. These components or internals may be utilized in one or more of the embodiments described above. The refractory material has a melting point of no less than 2060° C. and which remains in oxide form when exposed to a gas having carbon partial pressure of $10^{-22}$ bar and oxygen partial pressure of $10^{-10}$ bar, measured at a temperature of 1200° C., wherein the refractory material has not less than 4 vol % formed porosity, measured at 20° C., based upon the bulk volume of the refractory material; may have a total porosity in the range of from 4 vol % to 60 vol %; may have a formed porosity is determined after sintering at a temperature of not less than 1700° C. for not less than one hour; may have a formed porosity in the range of from 5 vol % to 30 vol %; may have a total porosity in the range of from 5 vol % to 35 vol %; may have a formed porosity that comprises the total of both a formed vacant pore fraction and a formed durable component pore fraction; may include a multimodal grain size distribution including a first grain mode and a second grain mode, the D50 grain size of the first grain mode is not less than three times the D50 grain size of the second grain mode, wherein the formed pores have a D50 diameter in a size range of from not less than the D50 grain size of the second grain mode up to two times the D50 grain size of the first grain mode; may have a formed porosity comprises from 30% to 100% of the total porosity; may have a formed porosity that is created using at least one of a sacrificial voiding agent, a durable voiding agent, and a combination of sacrificial and durable voiding agent, wherein the voiding agent may comprise at least one of a sacrificial polymeric material, a hollow particle, and a solid particle; may have at least 50% of the formed pores have a three-dimensional body factor of not greater than 2.5; may have a melting point of not less than 2160° C.; may remain in the oxide form when exposed to a gas having a carbon partial pressure of $10^{-14}$ bar and oxygen partial pressure of $10^{-10}$ bar, measured at a temperature of 2000° C.; may have a crystalline structure is cubic during heat-up from 1250° C. to 2250° C.; may have a vapor pressure that is $\leq 10^{-7}$ bar at 2000° C.; may have a thermal shock resistance rating that demonstrates a total crack length per unit area after quenching the reactor component from 1100° C. into a water bath to a temperature of 50° C. is not greater than 30 cm/cm$^2$; may have a modulus of rupture mechanical flexural strength of not less than 13.8 MPa at a temperature in a range of from 1000° C. to 2000° C.; may include at least 50 wt % yttrium oxide (yttria) based upon the total weight of the refractory material; may substantially exclude oxides of toxic ceramics, wherein the oxides of toxic ceramics include beryllium and thorium; may include (i) at least 20 wt % of a first grain mode based upon the total weight of the refractory material, the first grain mode having a D50 grain size in the range of from 5 μm to 2000 μm, and (ii) at least 1 wt % of second grain mode based upon the total weight of the refractory material, the second grain mode having a D50 grain size in the range of from 0.01 μm up to not greater than one-fourth the D50 grain size of the first grain mode; or may include at least one of yttria, another yttrium containing compound, a zirconium containing compound, and combinations thereof. The formed pores may have a D50 diameter not less than the D50 grain size of the refractory material; may have a D50 diameter in a size range of from not less than the D50 grain size of the refractory material up to five times the D50 grain size of the refractory material; or may have a D50 diameter in a range of from not less than 1.5 times the D50 grain size of the second grain mode up four times the D50 grain size of the second grain mode.

Further, in other embodiments, flue gas from the combustion stage in the reactor may be recycled to the combustion inlet and mixed with air to provide a preferred oxygen content in the regeneration-stage feed. Low-oxygen flue gas may also be useable as a purge stage before sending hydrocarbon vapor feed to the reactor in other embodiments.

The embodiments of the present techniques may also comprise different embodiments, such as in the following exemplary paragraphs:

1. A hydrocarbon conversion method comprising: exposing a pyrolysis feed to thermal pyrolysis high-severity operating conditions including a peak pyrolysis gas temperature ≥1540.0° C. to produce a reactor product that comprises ethylene and acetylene and that has an $C_{3+}$ to acetylene weight ratio ≤0.5; removing from the reactor product a first product comprising tars and/or solids; and converting at least a portion of the reactor product's acetylene to ethylene, wherein the converting is downstream of the removing.

2. The method of paragraph 1, wherein the $C_{3+}$ to acetylene weight ratio is ≤0.45.

3. The method of any one of paragraphs 1 or 2, wherein the pyrolysis feed comprises hydrocarbons and has a hydrogen to carbon ($H_2$/C) ratio in the range of 0.1 to 5.0.

4. The method of any one of paragraphs 1 to 3, further comprising polymerizing at least a portion of the ethylene.

5. The method of any one of paragraphs 1 to 4, further comprising compressing at least a portion of the reactor product upstream of the converting.

6. The method of any one of paragraphs 1 to 5, further comprising separating nitrogen from the reactor product.

7. The method of any one of paragraphs 1 to 6, further comprising separating hydrogen from the reactor product upstream of the converting.

8. The method of any one of paragraphs 1 to 7, further comprising separating hydrogen downstream of the converting.

9. The method of any one of paragraphs 7 to 8, wherein the hydrogen is separated via one or more of a hydrogen membrane, pressure swing adsorption, electrochemical, cryogenic separation or solvent absorption.

10. The method of any one of paragraphs 7 to 9, further comprising adding a combustion feed to at least a portion of the separated hydrogen and reacting the combustion feed along with the at least a portion of the separated hydrogen in a thermal pyrolysis reactor to provide heat for the thermal pyrolysis high-severity operating conditions.

11. The method of any one of paragraphs 7 to 9, wherein the pyrolysis feed is derived from at least a portion of the separated hydrogen.

12. The method of any one of paragraphs 7 to 9, comprising adding a combustion feed to a first portion of the separated hydrogen and reacting the combustion feed along with the first portion of the separated hydrogen in a thermal pyrolysis reactor and deriving the pyrolysis feed from a second portion of the separated hydrogen.

13. The method of any one of paragraphs 7 to 9 comprising adding at least a portion of the separated hydrogen to at least a portion of the reactor product's acetylene, at least a portion of the converting being conducted in an acetylene converter unit.

14. The method of any one of paragraphs 1 to 13, wherein the peak pyrolysis gas temperature is in the range of 1540.0°

C. to 2200.0° C., and wherein the exposing is for a residence time in the range from 0.5 second to 0.001 second.

15. The method of any one of paragraphs 1 to 13, wherein the peak pyrolysis gas temperature is in the range of 1600.0° C. to 1800.0° C., and wherein the exposing is for a residence time in the range from 0.5 second to 0.001 second.

16. The method of any one of paragraphs 1 to 15, wherein the exposing is performed within a regenerative reactor.

17. The method of any one of paragraphs 1 to 16, wherein the wherein the exposing is performed within a regenerative reverse flow reactor.

18. The method of paragraph 17, wherein the regenerative reverse flow reactor comprises a reactor body, wherein the reactor body forms a reaction region within the reactor body; a packing material disposed at least partially within the reaction region; and one or more poppet valve assemblies coupled to the reactor body and in flow communication with the reaction region and controlling fluid flow of the at least a portion of the pyrolysis feed between a location external to the reactor body and within the reaction region.

19. The method of any one of paragraphs 17 or 18, further comprising: exothermically reacting a first combustion feed with a second combustion feed to heat a region at least partially within the regenerative reverse flow reactor; removing combustion products from the regenerative reverse flow reactor; and heating the pyrolysis feed using at least a portion of the heat generated by the exothermic reaction.

20. The method of paragraph 19, further comprising purging the heated region with a vapor purge stream after the removing the combustion products and prior to passing the pyrolysis feed into the heated region.

21. The method of any one of paragraphs 19 to 20, wherein the first combustion feed and the second combustion feed are separately heated within the regenerative reverse flow reactor prior to exothermically reacting in the region.

22. The method of any one of paragraphs 19 to 21, wherein the combustion and pyrolysis in the regenerative reverse flow reactor are conducted in sequence, the sequence having a cycle time in the range of 0.5 seconds to 30 seconds.

23. The method of any one of paragraphs 19 to 22, wherein the reactor product is quenched within the regenerative reverse flow reactor in the absence of any added fluid.

24. The method of any one of paragraphs 1 to 23, further comprising deriving the pyrolysis feed and a bottoms product from a hydrocarbon feed prior to the exposing.

25. The method of paragraph 24, wherein the hydrocarbon feed comprises ≥90.0 wt. % of crude oil or crude oil components, based on the weight of the hydrocarbon feed.

26. The method of any one of paragraphs 1 to 23, wherein the pyrolysis feed comprises ≥90.0 wt. % methane, based on the weight of the pyrolysis feed.

27. An apparatus for processing hydrocarbons comprising: a thermal pyrolysis reactor configured to expose a pyrolysis feed to high-severity operating conditions including a peak pyrolysis gas temperature ≥1540.0° C. within the thermal pyrolysis reactor to produce a reactor product that comprises ethylene and acetylene and that has an $C_{3+}$ to acetylene weight ratio ≤0.5; a solids removal unit in fluid communication with the thermal pyrolysis reactor and configured to separate a bottoms product comprising tars and/or solids from the reactor product produced in the thermal pyrolysis reactor; and an acetylene converter in fluid communication with the solids removal unit and configured to convert the at least a portion of the reactor product's acetylene into ethylene.

28. The apparatus of paragraph 27, further comprising a polymerization unit in fluid communication with the acetylene converter, the polymerization unit being configured to convert at least a portion of the ethylene into polyethylene.

29. The apparatus of any one of paragraphs 27 to 28, further comprising a compressor in fluid communication with the solids removal unit, the compressor being configured to compress at least a portion of the reactor product.

30. The apparatus of any one of paragraphs 27 to 29, further comprising a nitrogen separation unit in fluid communication with the acetylene converter, the nitrogen separation unit being configured to separate nitrogen from at least a portion of the reactor product.

31. The apparatus of any one of paragraphs 27 to 30, further comprising a hydrogen separation unit in fluid communication with the acetylene converter, the hydrogen separation unit being configured to separate a hydrogen product from at least a portion of the reactor product prior to the acetylene converter.

32. The apparatus of any one of paragraphs 27 to 31, further comprising a hydrogen separation unit in fluid communication with the acetylene converter, the hydrogen separation unit being configured to separate a hydrogen product from the ethylene product.

33. The apparatus of any one of paragraphs 31 to 32, wherein the hydrogen separation unit comprises at least one of a hydrogen membrane, a pressure swing adsorption unit, an electrochemical unit, a cryogenic separation unit, a solvent absorption unit or any combination thereof.

34. The apparatus of any one of paragraphs 31 to 33, further comprising one or more lines providing fluid communication between the hydrogen separation unit and the thermal pyrolysis reactor at least one line being configured to provide a portion of the hydrogen product to a combustion feed being provided to the thermal pyrolysis reactor, wherein the thermal pyrolysis reactor is configured to react the portion of the hydrogen product and the combustion feed to heat the thermal pyrolysis reactor.

35. The apparatus of any one of paragraphs 31 to 33, further comprising one or more lines providing fluid communication between the hydrogen separation unit and the thermal pyrolysis reactor, at least one line being configured to combine a portion of the hydrogen product with a reactor feed prior to heating the pyrolysis feed in the thermal pyrolysis unit.

36. The apparatus of any one of paragraphs 31 to 33, further comprising (i) one or more lines providing fluid communication between the hydrogen separation unit and the thermal pyrolysis reactor, at least one line being configured to provide a first portion of the hydrogen product to a combustion feed being provided to the thermal pyrolysis reactor and (ii) one or more lines providing fluid communication between the hydrogen separation unit and the thermal pyrolysis reactor, at least one of the lines being configured to combine a second portion of the hydrogen product to a reactor feed prior to heating the pyrolysis feed in the thermal pyrolysis unit.

37. The apparatus of any one of paragraphs 31 to 33, further comprising one or more lines for providing a portion of the hydrogen product to the acetylene converter.

38. The apparatus of any one of paragraphs 27 to 37, wherein the thermal pyrolysis reactor is configured to expose the pyrolysis feed to the peak pyrolysis gas temperature in the range of 1540.0° C. to 2200.0° C., and maintain the at least a portion of the pyrolysis feed within the thermal pyrolysis reactor for a residence time in the range of 0.5 seconds and 0.001 second.

39. The apparatus of any one of paragraphs 27 to 37, wherein the thermal pyrolysis reactor is configured to expose the at least a portion of the pyrolysis feed to the peak pyrolysis gas temperature from 1600.0° C. to 1800.0° C., and maintain the at least a portion of the pyrolysis feed within the thermal pyrolysis reactor for a residence time in the range of 0.5 seconds and 0.001 second.

40. The apparatus of any one of paragraphs 27 to 39, wherein the thermal pyrolysis reactor is a regenerative reactor.

41. The apparatus of any one of paragraphs 27 to 39, wherein the thermal pyrolysis reactor is a regenerative reverse flow reactor.

42. The apparatus of paragraph 41, wherein the regenerative reverse flow reactor comprises:
a reactor body, wherein the reactor body forms a reaction region within the reactor body;
a packing material disposed at least partially within the reaction region; and
one or more valve assemblies coupled to the reactor body and in flow communication with the reaction region, the reactor bodies being configured to control fluid flow of the at least a portion of the pyrolysis feed between a location external to the reactor body and within the reaction region.

43. The apparatus of paragraph 42, wherein the one or more valve assemblies comprise one or more poppet valve assemblies.

44. The apparatus of paragraph 27, further comprising a feed separation unit in fluid communication with the thermal pyrolysis reactor, the feed separation unit being configured to separate a feed into the pyrolysis feed and bottoms product prior to providing the pyrolysis feed to the thermal pyrolysis reactor.

45. The apparatus of any one of paragraphs 27 to 44, wherein the thermal pyrolysis reactor comprises one or more components internal to the thermal pyrolysis reactor, the internal components being formed from materials substantially made of an oxide material that is chemically stable under pyrolysis conditions and has a melting point ≥2100° C.

46. The apparatus of any one of paragraphs 27 to 44, wherein the thermal pyrolysis reactor comprises one or more components internal to the thermal pyrolysis reactor formed substantially from a ceramic material, wherein the ceramic material comprises a multimodal grain distribution including; (i) at least 50 wt % of coarse grains including a metal oxide, the coarse grains comprising a D50 grain size in the range of from 5 to 800 (m, based upon the total weight of the component; and (ii) at least 1 wt % of fine grains comprising a D50 average grain size not greater than one-fourth the D50 grain size of the coarse grain, dispersed within the coarse grains, based upon the total weight of the component; wherein after sintering, the component has porosity at ambient temperature in the range of from 5 to 45 vol. %, based on the volume of the formed component.

47. The apparatus of any one of paragraphs 27 to 45, wherein the thermal pyrolysis reactor comprises one or more components internal to the thermal pyrolysis reactor formed substantially from a refractory material, wherein the refractory material comprises (i) at least 20 wt % of a first grain mode based upon the total weight of the refractory material, the first grain mode comprising yttria having a D50 grain size in the range of from 5 to 2000 (m, the yttria including a matrix oxide stabilizer; (ii) at least 1 wt % of a second grain mode having a D50 grain size in the range of from 0.01 (m up to not greater than one-fourth the D50 grain size of the first grain mode yttria, based upon the total weight of the refractory material; and (iii) the refractory material comprising at least 1 wt % of a preservative component; wherein after sintering the material has porosity at 20° C. of from 5 to 45 vol %.

48. The apparatus of any one of paragraphs 27 to 45, wherein the thermal pyrolysis reactor comprises one or more components internal to the thermal pyrolysis reactor formed from a refractory material of yttria, wherein the refractory material comprises at least 21 wt % yttria based upon the total weight of the refractory material.

49. The apparatus of any one of paragraphs 27 to 45, wherein the thermal pyrolysis reactor includes at least one internal component, the internal component comprising at least one formed refractory material in oxide form, wherein the refractory material has a melting point ≥2060° C. and which remains in oxide form when i) exposed to a first gas at a first temperature, the first gas having (a) an oxygen partial pressure of $10^{-15}$ bar and (b) a carbon partial pressure greater than that at which zirconium oxide changes phase to zirconium carbide at the first temperature; wherein the first temperature is less than that of zirconium's triple point at the oxygen partial pressure; and/or ii) exposed to a second gas having the oxygen partial pressure at a second temperature, the second temperature being greater than or equal to that of zirconium's triple point at the oxygen partial pressure.

While the present invention has been described and illustrated with respect to certain embodiments, it is to be understood that the invention is not limited to the particulars disclosed and extends to all equivalents within the scope of the claims.

The invention claimed is:
1. A hydrocarbon conversion method comprising:
exposing a pyrolysis feed in a regenerative reverse flow reactor to thermal pyrolysis high-severity operating conditions including a peak pyrolysis gas temperature ≥1540.0° C., a pressure ≥44 psig, and a residence time in the range of about 4 to about 53 milliseconds to produce a reactor product that comprises ethylene and acetylene and that has a $C_{3+}$ yield ≤13.7 wt. %, a $C_{3+}$ to acetylene weight ratio in the range of from 0.261 to 0.5;
removing from the reactor product a first product comprising tars, solids, or mixtures thereof; and converting at least a portion of the acetylene in the reactor product to ethylene, wherein the converting is downstream of the removing.

2. The method of claim 1, wherein the pyrolysis feed (i) comprises ≥50.0 wt. % hydrocarbons based on the weight of the pyrolysis feed and (ii) has a hydrogen to carbon ($H_2/C$) ratio in the range of 0.1 to 5.0.

3. The method of claim 1, further comprising polymerizing at least a portion of the ethylene.

4. The method of claim 1, further comprising compressing at least a portion of the reactor product upstream of the converting.

5. The method of claim 1, further comprising separating hydrogen from the reactor product upstream and/or downstream of the converting.

6. The method of claim 5, wherein the hydrogen is separated via hydrogen membrane, pressure swing adsorption, electrochemical separation, cryogenic separation or solvent absorption, or combinations thereof.

7. The method of claim 5, further comprising adding a combustion feed to at least a portion of the separated hydrogen and reacting the combustion feed along with the at least a portion of the separated hydrogen in the regenerative reverse flow reactor to provide heat for the thermal pyrolysis high-severity operating conditions.

8. The method of claim 5, wherein the pyrolysis feed is derived from at least a portion of the separated hydrogen.

9. The method of claim 5, further comprising adding a combustion feed to a first portion of the separated hydrogen and reacting the combustion feed along with the first portion of the separated hydrogen in the regenerative reverse flow reactor and deriving the pyrolysis feed from a second portion of the separated hydrogen.

10. The method of claim 5 wherein the conversion of the at least a portion of the acetylene takes place in an acetylene converter unit, and further comprising adding at least a portion of the separated hydrogen to the acetylene converter unit.

11. The method of claim 1, wherein the peak pyrolysis gas temperature is in the range of 1600.0° C. to 1800.0° C.

12. The method of claim 1, wherein the regenerative reverse flow reactor comprises (i) a reactor body, wherein the reactor body forms a reaction region within the reactor body; (ii) a packing material disposed at least partially within the reaction region; and (iii) one or more poppet valve assemblies coupled to the reactor body and in flow communication with the reaction region, and further comprising controlling fluid flow of at least a portion of the pyrolysis feed between a location external to the reactor body and within the reaction region.

13. The method of claim 1, wherein the reactor product has a ratio of ethylene to acetylene (E/A ratio) of ≥about 0.15 (wt/wt).

14. The method of claim 1, wherein the pressure is ≥103 psig.

* * * * *